United States Patent
Coberley et al.

(10) Patent No.: US 7,428,554 B1
(45) Date of Patent: Sep. 23, 2008

(54) SYSTEM AND METHOD FOR DETERMINING MATCHING PATTERNS WITHIN GENE EXPRESSION DATA

(75) Inventors: Carter Coberley, Hagerstown, MD (US); James C. Diggans, Germantown, MD (US); Doug Dolginow, Potomac, MD (US); Michael Elashoff, Germantown, MD (US); Larry Mertz, Rockville, MD (US)

(73) Assignee: Ocimum Biosolutions, Inc., Gaithersburg, MD (US)

( * ) Notice: Subject to any disclaimer, the term of this patent is extended or adjusted under 35 U.S.C. 154(b) by 476 days.

(21) Appl. No.: 10/850,232

(22) Filed: May 20, 2004

Related U.S. Application Data

(63) Continuation-in-part of application No. PCT/US02/35454, filed on Nov. 4, 2002, and a continuation-in-part of application No. 10/090,144, filed on May 23, 2001, now abandoned, which is a continuation-in-part of application No. 09/862,424, filed on May 23, 2001, now abandoned.

(60) Provisional application No. 60/471,826, filed on May 20, 2003, provisional application No. 60/536,389, filed on Jan. 14, 2004, provisional application No. 60/331,182, filed on Nov. 9, 2001, provisional application No. 60/388,745, filed on Jun. 17, 2002, provisional application No. 60/390,608, filed on Jun. 21, 2002, provisional application No. 60/412,156, filed on Sep. 19, 2002, provisional application No. 60/206,571, filed on May 23, 2000, provisional application No. 60/275,465, filed on Mar. 5, 2001.

(51) Int. Cl.
*G06F 17/30* (2006.01)
*G06F 17/00* (2006.01)

(52) U.S. Cl. .................................. 707/104.1; 707/3

(58) Field of Classification Search ............ 707/104.1, 707/3, 35; 702/19
See application file for complete search history.

(56) References Cited

U.S. PATENT DOCUMENTS 5,577,239 A 11/1996 Moore et al.

(Continued)

FOREIGN PATENT DOCUMENTS

| EP | 1 213 665 A2 | 6/2002 |
| WO | WO 01/73587 A2 | 10/2001 |
| WO | WO 03/001335 | 1/2003 |
| WO | WO 03/042780 | 5/2003 |

OTHER PUBLICATIONS

Paton et al., "Query Processing in the TAMBIS Bioinformatics Source Integration System," *Proceedings of the 11th International Conference on Scientific & Statistical Database Management*, Jul. 28-30, 1999, pp. 138-147.

(Continued)

*Primary Examiner*—Charles Rones
*Assistant Examiner*—Fariborz Khoshnoodi
(74) *Attorney, Agent, or Firm*—Procopio, Cory, Hargreaves & Savitch, LLP

(57) ABSTRACT

A computer-based system and method are provided for retrieving information from a number of data sources on a computer network containing biological data. The network database is organized in a b-tree configuration having a plurality of sample nodes. Each sample node includes a curated data set of pre-formatted and pre-computed summary biological data obtained from at least one biological sample. The plurality of sample nodes are organized in a hierarchical arrangement according to clinical relevance. A set of attributes is assigned to each sample node to facilitate navigation through the database using a browser accessible through a graphical user interface. The set of attributes including at least one taxonomy designation selected from the group including tissues, diseases, medications and sample parameters. Search results that are produced include automated reports of the summary biological data stored in the sample nodes and custom reports generated using the summary biological data.

49 Claims, 13 Drawing Sheets

U.S. PATENT DOCUMENTS

| | | | |
|---|---|---|---|
| 5,701,467 A * | 12/1997 | Freeston | 707/100 |
| 5,758,026 A * | 5/1998 | Lobley et al. | 706/11 |
| 6,484,166 B1 | 11/2002 | Maynard | |
| 6,493,637 B1 * | 12/2002 | Steeg | 702/19 |
| 6,519,631 B1 | 2/2003 | Rosenschein et al. | |
| 6,523,041 B1 | 2/2003 | Morgan et al. | |
| 2001/0047353 A1 * | 11/2001 | Talib et al. | 707/3 |
| 2002/0194187 A1 | 12/2002 | McNeil et al. | |
| 2003/0009295 A1 | 1/2003 | Markowitz | |
| 2003/0100999 A1 | 5/2003 | Markowitz | |
| 2003/0171876 A1 | 9/2003 | Markowitz | |

OTHER PUBLICATIONS

Davidson et al , "BioKleisli A Digital Library for Biomedical Researchers", *International Journal on Digital Libraries,* Aug. 12, 1996, pp. 36-53, vol. 1, No. 1.

* cited by examiner

| | (OVARY, NOS) AND (MALIGNANT NEOPLASM OF OVARY) AND (CLEAR CELL ADENOCARCINOMA, NOS) | | | | | | | | |
|---|---|---|---|---|---|---|---|---|---|
| Sample Or GeneChip | AvgCorr | %Present | β-Actin | GAPDH | SF | RawQ | %Sat | Total | Is Outlier? |
| 1 | 0.88 | 0 | 0 | 0 | 0 | 0 | 0 | 0 | No |
| 2 | 0.88 | 0 | 0 | 0 | 0 | 0 | 0 | 0 | No |
| 3 | 0.87 | 0 | 0 | 0 | 0 | 0 | 0 | 0 | No |
| 4 | 0.81 | 0 | 0 | 0 | 0 | 0 | 0 | 0 | No |
| 5 | 0.81 | 0 | 1 | 0 | 0 | 1 | 1 | 3 | Yes |
| 6 | 0.87 | 0 | 0 | 0 | 0 | 0 | 0 | 0 | No |
| 7 | 0.78 | 0 | 0 | 0 | 0 | 0 | 0 | 0 | No |
| 8 | 0.86 | 0 | 0 | 0 | 0 | 0 | 0 | 0 | No |

Figure 3

| Gene | Comparison | Control Mean | Experimental Mean | Fold Change | T-Statistic |
|---|---|---|---|---|---|
| $G_1$ | $C_1$ | 100 | 300 | +3 | 4.5 |
| $G_1$ | $C_2$ | 500 | 50 | -10 | 4.2 |
| $G_2$ | $C_1$ | 1000 | 2000 | +2 | 5.3 |
| $G_3$ | $C_2$ | 50 | 150 | +3 | 3.2 |
| $G_3$ | $C_3$ | 75 | 5 | -15 | 2.8 |
| ... | ... | ... | ... | ... | ... |
| $G_n$ | $C_n$ | ... | ... | ... | ... |

Figure 4a

| | $C_1$ | $C_2$ | $C_3$ | ... | $C_n$ |
|---|---|---|---|---|---|
| $G_1$ | +1 | -1 | 0 | ... | ... |
| $G_2$ | +1 | 0 | 0 | ... | ... |
| $G_3$ | 0 | +1 | -1 | ... | ... |
| ... | ... | ... | ... | ... | ... |
| $G_n$ | ... | ... | ... | ... | ... |

Figure 4b

Sample Set Report — Breast: Infiltrating Ductal Carcinoma—Smoking

Pathology Detail | Gene X

Sort By: Present Frequency

Note: Use Export to get the full results. The table shown here represents only the top 1% of the gene expression data for this sample.

| Affy ID | Symbol | Description | Pres. Freq | Present | Marginal | Absent | Mean | StdDev | Median |
|---|---|---|---|---|---|---|---|---|---|
| AFFX-BioB-5_at | | | 0.9987 | 80% | 0% | 20% | 145.56 | 34.34 | 131.43 |
| AFFX-BioB-M_at | | | 0.9991 | 100% | 0% | 0% | 352.56 | 76.24 | 341.78 |
| 31637_s_at | | | 0.4016 | 50% | 10% | 40% | 210.56 | 47.24 | 192.61 |
| 32402_s_at | SPK | symplekin; Huntingtin interacting protein I | 0.1915 | 20% | 10% | 70% | 65.24 | 13.86 | 72.63 |
| 222380_s_at | NR1D1 | nuclear receptor subfamily 1, group D, member 1 | 0.8467 | 90% | 0% | 10% | 457.32 | 180.26 | 521.89 |
| 222383_s_at | ALOXE3 | arachidonate lipoxygenase 3 | 0.0071 | 5% | 0% | 95% | 15.3 | 4.8 | 17.24 |
| AFFX-BioB-5_at | | | 0.9987 | 80% | 0% | 20% | 145.56 | 34.34 | 131.43 |
| AFFX-BioB-M_at | | | 0.9991 | 100% | 0% | 0% | 352.56 | 76.24 | 341.78 |
| 31637_s_at | | | 0.4016 | 50% | 10% | 40% | 210.56 | 47.24 | 192.61 |
| 32402_s_at | SPK | symplekin; Huntingtin interacting protein I | 0.1915 | 20% | 10% | 70% | 65.24 | 13.86 | 72.63 |
| 222380_s_at | NR1D1 | nuclear receptor subfamily 1, group D, member 1 | 0.8467 | 90% | 0% | 10% | 457.32 | 180.26 | 521.89 |
| 222383_s_at | ALOXE3 | arachidonate lipoxygenase 3 | 0.0071 | 5% | 0% | 95% | 15.3 | 4.8 | 17.24 |

New Tracker

Tracker Items
Genes (4 items)
- NOTCH2 – Homolog 2 Vari...
- KINM7 – Gene Description...
- ☑ HELIOS – Gene Description...

Gene Families (Empty)

Pathways (4 Items)
- CARM1 and Regulation of t...
- ☑ KLINK monical wearing col...
- MANET flat aspect impressi...
- TMBG accordian playing pun...

Sample Sets (10 items)
- Colon: Normal
- Colon: Crohn's Disease
- Breast: Normal
- ☑ Breast: Infiltrating Ductal Car...
- ☑ Breast: Infiltrating Ductal Car...
- Kidney: Normal
- ☑ Liver: Cancer Type 3 – Stage...
- Liver: Normal

Custom Report

Gene(s) Selected: HELIOS
Sample Set(s) Selected: Breast: Infiltr...
Liver: Cancer Type 3 Stag...criminal Genes + Samples = Results
- eNorthern
- Diff-X
- Gene Detail
- Pathology Detail

Fig. 13

SYSTEM AND METHOD FOR DETERMINING MATCHING PATTERNS WITHIN GENE EXPRESSION DATA

RELATED APPLICATIONS

This application claims priority of U.S. Provisional Application Nos. 60/471,826, filed May 20, 2003, and No. 60/536,389, filed Jan. 14, 2004. This application is a continuation-in-part of International Patent Application No. PCT US02/35454, filed Nov. 4, 2002, which claims priority to U.S. Provisional Applications No. 60/331,182, filed Nov. 9, 2001, No. 60/388,745, filed Jun. 17, 2002, No. 60/390,608, filed Jun. 21, 2002, and No. 60/412,156, filed Sep. 19, 2002. This application is also a continuation-in-part of U.S. patent application Ser. No. 10/090,144, filed Mar. 5, 2002, now abandoned which claims priority of provisional application Ser. No. 60/275,465, filed Mar. 5, 2001, and which is a continuation-in-part of application Ser. No. 09/862,424, filed May 23, 2001, now abandoned which claims priority of provisional application Ser. No. 60/206,571, filed May 23, 2000. Each identified application is incorporated herein by reference in its entirety for all purposes.

FIELD OF THE INVENTION

The present invention relates generally to systems and methods for organizing biological data for efficient exploration and analysis. More particularly, the invention relates to a system and method for organizing gene expression and clinical data for facilitating data mining by classifying the data into categories of sample sets, curating such sets, and pre-computing comparisons between selected sample sets.

BACKGROUND OF THE INVENTION

Using current DNA microarray technology, researchers and clinicians are able to easily collect large amounts of data to indicate which genes or ESTs (expressed sequence tags) are regulated upwards or downwards during various disease states, following various pharmacological treatments, or following exposure to a variety of toxicological insults. The relevance of this gene expression data is often determined by its relationship to other information within the context of the current analysis. For example, knowing that there is an increased expression of a particular gene or EST during the course of a disease is important information. In addition, there is a need to correlate this data with various types of clinical data, for example, a patient's age, sex, weight, genetic, environmental and behavioral history, stage of clinical development, stage of disease progression etc. What is needed is a way to correlate the vast amounts of gene and EST expression data that are available from DNA microarrays with the corresponding clinical data from the samples that are tested. As used herein, the term "gene" or "gene expression" will also include (EST" or "EST expression, unless otherwise indicated.

Researchers wish to answer questions such as: 1) which genes are expressed in cells of a malignant tumor but not expressed in either healthy tissue or tissue treated according to a particular regime; 2) which genes or ESTs are expressed in particular organs but not in others; and 3) how is a gene-of-interest regulated across a comprehensive panel of diseases and therapeutic areas with respect to human systems biology? A better understanding of the complex network of gene interactions can lead to discovery of novel therapeutic mechanisms and identify and prioritize potential drug targets with respect to specific therapeutic and large-scale biological considerations.

Traditional sample-based analysis methods for gene expression data involve manual curation of sample sets. Investigators begin their analysis with a specific goal (e.g., "today I will investigate Alzheimer's disease") in mind and build the sample sets accordingly. This method biases the resulting analyses towards the initial goal of the investigator and leaves potentially interesting patterns undiscovered because the investigator did not have time to manually exhaust all potential analysis routes through the available data. To provide an example, discovering a gene regulated in Alzheimer's disease is interesting; but finding a gene regulated across all known degenerative neural diseases is potentially far more useful.

Commercially-available databases have been created containing massive amounts of annotated gene expression data derived from clinically important tissues, both normal and diseased, which can be searched for identifying relationships between specific genes and resulting proteins, e.g., those that are involved in a disease pathway. These databases are managed to enhance accuracy and reliability and to ensure that the data are regularly updated to include the latest developments in the field. Internet links are provided to provide easy access to related data contained in public databases. Graphics tools can be linked to enable visualization of the results. (See, e.g., International Publication No. WO 02/071059, published 9 Sep. 2002, assigned to the present assignee. The disclosure of this publication is incorporated herein by reference in its entirety.) Exemplary of such commercial databases are the GeneExpress® line of products available from Gene Logic Inc., Gaithersburg, Md., which utilizes the Affymetrix Gene-Chip® microarray data and its sample identification standards. Typically, such databases are used for evaluation of a researcher's manually curated sample and gene sets, e.g., manually-selected sets of samples from specific microarray sets, tissue types, pathology/morphology, etc. Often, the researcher will use the curated sample (or gene) set to compare his or her own laboratory results from tests performed using GeneChip® microarrays with gene expression data and corresponding sample information extracted from the existing database. Such analysis generally requires a fairly high level of sophistication in dealing with microarray-based data analysis, since individual samples and/or genes must be selected for inclusion in the sample sets. If the search queries are not carefully tailored, the search may become mired in the huge volume of data that must be searched. Once the search is completed, additional downstream data synthesis is usually required for interpretation of the search results.

While customization of the search strategy at the sample or gene level can be a valuable discovery tool, many researchers may be interested in investigating higher level relationships between disease pathology and genomics without the need for manually curating their own sample sets, interpreting the gene expression data or generating custom gene lists. This latter approach can be referred to as an "in silico experiment", where the data to be mined is pre-existing within the computer database and the "experiment" consists of selecting and/or making different combinations of data from the database based upon pathological and biological considerations, without inputting specific information about individual samples. Such an approach serves as a useful reference tool, however, without careful data management and organization, the researcher may run into problems such as slow computational response time, as well as the inability to recognize global gene expression patterns, due to the large volume of data to be searched and presented.

Accordingly, it would be desirable to provide a reference tool in which the database is organized to facilitate rapid query searching and subsequent data presentation. It is to such a system and method that the present invention is directed.

BRIEF SUMMARY OF THE INVENTION

The system and method for analysis of biological data according to the present invention avoid many burdensome requirements of existing methods by allowing the user to define more general sample relationships based on specific therapeutic and large-scale human biological considerations.

The aforementioned needs are addressed by providing methods and systems that correlate normal and diseased tissues or cell lines from humans and model organisms with critical clinical findings and gene expression data, thereby improving target selection and prioritization. Additional variables for correlation include medications, patient secondary diagnosis, age, race, gender and lifestyle attributes (such as drug use, smoking, alcohol consumption, etc) and clinical diagnostic data (e.g., cholesterol levels, hematocrits, white blood cell counts, etc.) which can be compared within the framework provided herein. In addition, while the illustrative examples provided herein are derived from gene expression data analysis, data derived from measurement of other biological parameters can be included such as protein expression data (proteomic analysis), metabolite measurement (metabonomic analysis) as well as data resulting from the assay of other clinically and biologically relevant biomolecules. Accordingly, the present invention is not intended to be limited solely to the mining of information from gene expression data, but is suitable for use with a broader range of biological data types.

The system and method of the present invention provide the ability to examine the effects of therapeutic and prophylactic compounds on human and animal tissues or cell lines. One can study the mechanism of action of therapeutic compounds and the characteristics of experimental model systems by comparing the gene expression data with known therapeutic and experimental parameters. Similarly, the present system allows one to examine the affects of toxic compounds on tissues and cells in both a pre-clinical and clinical setting.

An efficient and easy-to-use query system and data analysis scheme for a gene expression data source is provided. The present system and method permit large scale gene expression databases to be fully exploited. This query system and data analysis method can be implemented in any one of a number of computational programming languages and processes known to those in the art. Using such a system, one can easily identify genes, ESTs (expressed sequence tags), genes associated with biological pathways and gene families whose expression correlates to particular tissue or disease morphology type. Various tissue types may correspond to different diseases, states of disease progression, organs, species, etc.

In an exemplary embodiment, the gene expression database is organized using a hierarchical b-tree according to the descriptive and clinical sample attributes stored. Other sources of data such as text files containing tabular sample data may also be similarly organized. As is known in the art, a b-tree is a generic data structure with properties that make it useful for database storage and indexing. B-trees use nodes with many branches, and records are stored in locations called "leaves." The maximum number of branches per node provides the order of the tree. The b-tree algorithm minimizes the number of times a medium must be accessed to locate a desired record. The user defines attributes on which to filter for each level of the b-tree. The resulting leaf nodes of the tree then contain samples grouped according to pre-determined specifications. A simple search grammar can then be employed to arbitrarily group together leaf nodes depending on their attributes. These grouped leaf nodes are used as "control" and "experimental" sample sets. A t-test is performed to test for statistically significant correlation between the control and experimental sample sets.

In one embodiment, the results of the b-tree analysis are provided as a table of information that can be stored in an electronic spreadsheet (e.g., a Microsoft® Excels file), printed as a hardcopy or exported to commercially available data mining software tools such as Spotfire® (from Spotfire, Inc., Somerville, Mass.), Partek Pro® (from Partek Incorporated, St. Charles, Mo.), GeneSpring® (from Silicon Genetics, Redwood City, Calif.) and others for data mining and visualization. This is particularly helpful for more complex data sets composed of several genes, gene families or entire pathways.

In a preferred embodiment, using a b-tree configuration, data are pre-formatted and, in some cases, comparisons pre-computed, for producing rapid responses to searches based upon pathological or biological parameters. The "pre-formatting" of data is accomplished by organizing the data into granular sample nodes consisting of curated data sets that are categorized with respect to relevant pathological and biological considerations and summary gene expression values. Relevant statistics are included in each sample set. As a result of the pre-formatting, sample nodes may contain overlapping information since data contained within a given node may also be relevant to one or more other nodes. The sample nodes are maintained within a node database which can used as a staging area to document and inventory existing curated sample sets and new curated sample sets as they become available. Also included in the node database are sample set nomenclature for identifying the data sets and data therein along with an explanation of how and/or why the specific sample set was created. Curation of the sample data sets may be performed either manually or via a computer-implemented process. In either method, quality control filters are applied to exclude outlier data. Existing sample nodes are periodically updated to include new data, and new sample nodes may be created based upon newly identified relationships between existing and/or new data.

Pre-computed analyses of the data in different sample nodes are performed on a pairwise basis for nodes containing data which are commonly compared. For example, differential expression in diseased tissue versus normal tissue for a given tissue type would be a commonly-requested comparison, as would differential expression in diseased tissues corresponding to two different diseases of the same tissue type. This pre-computed data is also stored in the node database. In one embodiment, the comparison results can be stored in an N×N matrix where N is the number of nodes. However, since there are certain comparisons which do not make clinical or biological sense (e.g., normal pancreas versus kidney small cell carcinoma), not all comparisons are needed, and an alternate storage scheme would be appropriate to conserve database storage capacity. Nevertheless, the current invention also provides the researcher with the ability to create these custom comparisons should he or she choose to do so. Such comparison data cannot be pre-calculated and is, instead, achieved 'on the fly'.

The combination of sample nodes, pre-formatted data, and, where available, pre-computed comparisons stored in the node database permits a system user to rapidly access data via a user interface which is organized in a logical format corresponding to the different node categories. In an exemplary embodiment, the selection of the search flow begins with the user selecting one of broadest categories from the user interface options of genes, gene families, sample sets and pathways.

According to a first aspect of the present invention, in a computer system, a method is provided for retrieving information from a plurality of data sources containing biological data comprising: defining a plurality of sample nodes within the database, each sample node comprising a curated data set comprising a set of pre-formatted and pre-computed gene expression data obtained from at least one biological sample, wherein the plurality of sample nodes are organized in a hierarchical arrangement according to clinical relevance; assigning a set of attributes to each sample node, the set of attributes including at least one taxonomy designation selected from the group including tissues, diseases and medications; providing a user interface for entry of a search query and displaying search results, prompting entry of the search query by requesting user selection of a search category from the group including genes, gene families, pathways, and sample set taxonomy, and wherein each sample node of the plurality of sample nodes is associated with a plurality of search categories; searching the plurality of sample nodes for data responsive to the search query; selecting one or more sample nodes containing the data responsive to the search query; and generating a report of search results comprising the set of pre-formatted and pre-computed gene expression data responsive to the one or more selected sample nodes.

In a second aspect of the invention, the system comprises a search engine; a database comprising: a plurality of sample nodes, each sample node comprising a curated data set comprising a set of pre-formatted and pre-computed gene expression data obtained from at least one biological sample, wherein the plurality of sample nodes are organized in a hierarchical arrangement according to clinical relevance; a set of attributes assigned to each sample node, the set of attributes including at least one taxonomy designation selected from the group including tissues, diseases, medications or sample parameters; and a user interface for entry of a search query and displaying search results, wherein the search query comprises an instruction to the search engine to search a category from the group including genes, gene families, pathways, and sample set taxonomy, and wherein each sample node of the plurality of sample nodes is associated with a plurality of search categories.

In the preferred embodiment, user access is provided through an Internet web site onto which the user may log on at an Internet-capable work station or personal computer. The user is then instructed to select one of the threshold categories by selecting a tab tile from the options of genes, gene families, pathways and samples. Selection of one of the first three categories links the user to browser pages for queries based on specific gene information which can either be entered in a designated text box, e.g., entry of a sequence of the gene or entering a known public "token" identifier such as the GenBank accession number, or by selection of an option from a pull-down menu. The resulting report will depend on the selected category. Selection of the "sample" category takes the user to a page on which options are listed in a series of pull-down or scrolling input menus or check boxes that are arranged in tables which are to be addressed in order of increasing specificity. The threshold selection is the type of search, or taxonomy, which can be either tissue, disease, medication or sample parameter. Examples of sample parameters include gender, race, lifestyle attributes, clinical diagnostic data, etc. Then, the category of system type, e.g., cardiovascular system or central nervous system, and a subcategory, the choices of which depend on the threshold selection of the taxonomy. The sequence of selections has the goal of ultimately reaching the option of selecting from a set of choices corresponding to sample nodes. Since each sample node has already been defined, the corresponding data is rapidly retrieved from the node database for display in a "Sample Set Report" containing gene expression data and related information, including a text summary describing the sample. The selections within the "Sample" browser correspond to guided navigation of a pre-constructed b-tree in which all of the data has been classified into the nodes of the b-tree.

In a preferred embodiment, the user interface includes a tracking module, or "Tracker™", which allows the user to save selected items and generate custom reports by combining items saved in the module. Items that can be saved include sample sets, genes, gene families and pathways, each of which defines a separate category with the tracking module. The user will typically have multiple Tracker™ tracking modules, with the number of available trackers being virtually unlimited. Each tracker will contain items for a single species. The user may save, load, delete and create new Trackers, and may select one or more items for comparison for generating custom reports.

A further understanding of the nature and advantages of the inventions herein may be realized by reference to the remaining portions of the specification and the attached drawings.

BRIEF DESCRIPTION OF THE DRAWINGS

FIG. 3 provides an example of data generated from an outlier analysis detection and masking routine.

FIGS. 4a and 4b illustrate an example output from b-tree analysis in table form and the result of trinary (three-state) encoding of the b-tree output data, respectively.

FIG. 13 illustrates an exemplary GUI screen with a sample search result.

DETAILED DESCRIPTION OF THE PREFERRED EMBODIMENTS

Figure 1:
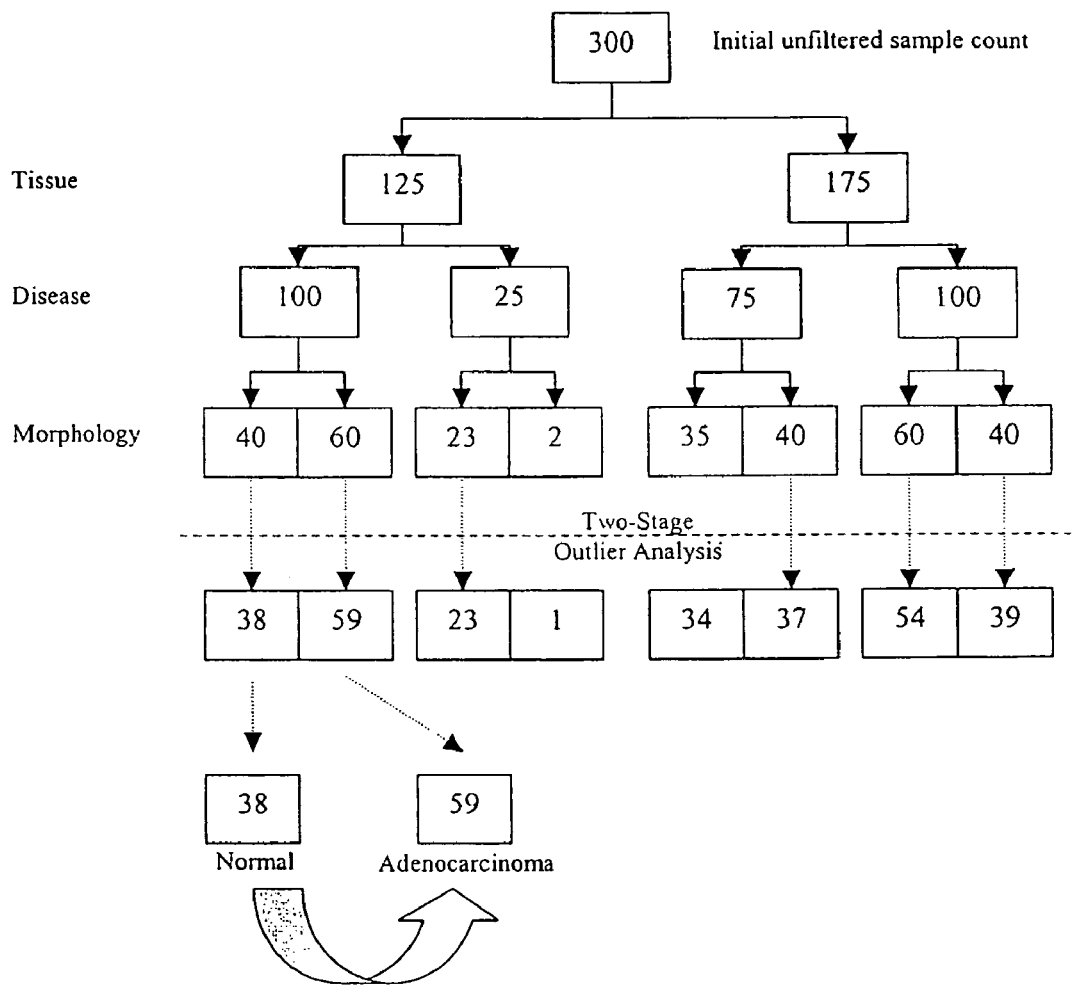
FIG. 1 illustrates an example of a b-tree structure for a user-defined tree dividing samples by tissue, then disease, then morphology.

The present invention uses a hierarchical method for organizing biological samples for analysis using a b-tree and a query grammar to manage and explore gene expression and related data. The results of the b-tree analysis are organized in a relational database to permit data mining for identification of interrelationships between behavior of different genes or gene fragments for, e.g., one or more diseases, treatments, or demographics.

According to the present invention, a computer system is designed for hierarchically organizing information regarding biological samples using an n-order b-tree and a query grammar. The method includes: providing a data source including gene expression data derived from sample based analyses; defining relationships between data based upon descriptive and clinical sample attributes; comparing a control sample set against an experimental sample set with regard to the defined relationship; and displaying the results of such comparison. In one embodiment this data source would be a relational database.

In an exemplary embodiment, the present system and method are related to a combined database and data mining algorithm and system such as disclosed in co-pending application Ser. No. 09/862,424, filed May 23, 2001, Ser. No. 10/018,461, filed Dec. 19, 2001, and Ser. No. 10/094,144, filed Mar. 5, 2002. The disclosure of each application is incorporated herein by reference in its entirety.

The database and analytical engine preferably run on hardware from Sun Microsystems, Inc. (Palo Alto, Calif.) on the Solaris™ 8 Operating Environment (also from Sun Microsystems). The database is Oracle Server 8.1.7.3. Other software includes Visibroker® C++3.3.2 from Borland Software Corporation (Scotts Valley, Calif.), Java 2 SDK version 1.3.1.03 (available on the WWW from Sun Microsystems), Apache HTTP server 1.3.12 and Xerces-c 1.7.0 XML parser, Expat 1.95.2 XML parser library, and Perl 5.6.0 and 5.6.1. For any of the identified software, later versions may be used as well. Supporting documentation for the hardware and each of the listed software programs is incorporated herein by reference for purposes of this disclosure.

In an embodiment of the present invention, gene expression data may be generated using the Affymetrix GeneChip® platform, marketed by Affymetrix Corporation of Santa Clara, Calif., and may be represented in the Genetic Analysis Technology Consortium ("GATC") relational format.

Samples are associated with attributes that describe properties useful for gene expression analysis. For example, sample structural and morphological characteristics (e.g., organ site, diagnosis, disease, stage of disease, etc.) and donor data (e.g., demographic and clinical record for human donors, or strain, genetic modification, and treatment information for animal donors). Samples may also be involved in studies and therefore can be grouped into several time/treatment groups.

An example includes the DONOR table. This table can include human donor attributes that span various domains: general attributes such as HEIGHT, WEIGHT, RACE, DATE_OF_BIRTH; deceased fields such as DEATH_CAUSE, DEATH_AGE; sparse data fields such as exercise habits, diet profile, sleeping and smoking habits, alcohol and any recreational drug habits.

The sample attributes can be organized into classification hierarchies implemented using controlled vocabularies or existing taxonomies such as the Systematized Nomenclature of Medicine ("SNOMED") topography and morphology axes, for sample organ and diagnosis, respectively.

The hierarchical organization of samples is accomplished using an n-order b-tree, essentially a hash, i.e., associative array, of references to sub-hashes. Each level in the tree is hashed on the sample attribute the user assigned to that particular level. The value stored for each key is a reference to the hash representing that portion of the next level down in the tree. The leaf nodes of the tree contain a count of samples belonging to that final node rather than a reference to any further tree levels. An example of this structure is diagrammed in FIG. 1, whereas the schema describing the overall application of this invention in the definition and retrieval of data from a large scale gene expression data source is diagrammed in FIG. 2.

In FIG. 1, the example tree is shown having two distinct tissue types, each with two distinct diseases, each disease with two distinct morphologies. The numbers in each box represent exemplary sample counts at each level. The illustrated b-tree is provided as an example only and is not intended to be limiting. Actual trees generated from a large data source are typically much larger, having upwards of 40 to 50 individual tissue types with multiple diseases and morphologies per tissue.

The hierarchical tree serves to define the general characteristics of the sample space and the possible routes through the sample space to collect valid sample sets. This first characteristic is used by the system to determine the number and nature of possible pair-wise comparisons to be made. The second characteristic is useful in a first-pass evaluation of sample set size and subsequent "pruning" of the tree (to remove sample sets not meeting minimum size requirements) in order to reduce the number of comparisons performed to only those considered to be "valid".

Automatically-generated sample sets tend to lack the level of curation possible in carefully annotated sets that are produced manually. In order to address this concern, the inventive system and method may employ two additional levels of filtering to further curate and trim the samples and/or leaf nodes of the tree. These processes involve evaluation of various quality control parameters related to GeneChip® microarray data. Samples or sample sets not meeting certain QC criteria can be trimmed from the analysis to bolster the quality of gene expression data for comparison. This provides users of such a system the benefits usually afforded by manual curation without the costly time investment.

Parameters evaluated by this sample set generation method, in a preferred embodiment using Affymetrix GeneChip® microarray data, include, but are not limited to, scale factor, raw-Q (a parameter indicating chip noise), the percentage of genes called present by Affymetrix algorithms, the percentage of saturated genes, and 5'/3' probe intensity ratios for the control genes GAPDH and $\beta$-actin. Within a sample set or leaf node of the tree, the mean or median value $\pm 3\sigma$ (standard deviations) for each of these parameters can be calculated (for example). In addition, contributions of these parameters to the QC process can be differentially weighted depending on the inherent effect each has on the microarray gene expression data.

Using a binary encoding scheme, each sample is given a score for each of six parameters. If, for each sample, a parameter value falls within the designated range it would be assigned a value of "0", whereas those parameters that fall outside the acceptable range would be assigned a value of "1" and labeled an "outlier" in that particular parameter.

A matrix can be generated for each sample set node of the tree listing these binary values with rows named by sample/GeneChip® microarray identifiers and columns named by parameter (see, e.g., FIG. 3). For each GeneChip® microarray, the number of failed parameters can be totaled and, if this number reaches a certain pre-defined level, decisions can be made to remove the sample from further analysis. FIG. 3 illustrates a sample data table generated during chip parameter outlier analysis. The AvgCorr column indicates the average correlation calculated for each sample drawn from a correlation matrix. Sample 5 (see column 1) registered a value of "1" for each of the parameters β-Actin (column 4), RawQ (column 7), and % Sat (column 8) for a total of value of 3 (column 9). As a result, sample 5 was declared an "outlier" and removed from the sample set and from all downstream analysis. If there are multiple GeneChip® microarrays for a particular sample, such as when running a sample across the Affymetrix Hu95 and Hu133 GeneChip® microarray sets, a decision can be made to remove one or more GeneChip® arrays from the analysis or even the entire sample, (composed of >1 GeneChip®0 arrays) if a significant number of microarrays assigned to that sample fail to meet the predetermined QC criteria.

In addition to curation of tree-node sample sets based on GeneChip® microarray performance parameters, it may also be desirable to trim samples that exhibit deviant biological behavior with respect to overall within-cohort gene expression measurements and patterns of the nodal sample set. Such samples could be simply misclassified or improperly coded in the database, or may possess unique clinical parameters not taken into account by the user's current b-tree sort order, such as percent tumor infiltration or alternative systemic secondary diseases. For such biological analyses, an automated approach utilizing, but not limited to, principal component analysis (PCA), leave-one-out (LOO) analysis, or partial least squares (PLS) analysis can be implemented to augment the statistical accuracy of automated sample set creation and curation.

PCA is a data-reduction technique known in the art that provides for the reduction of high-dimensional data into so-called 'principal components'. This technique is used within single sample sets to determine each sample's general similarity to other members within the group.

LOO analysis is used to determine, between any two sample sets, which samples in either set would, when removed, have a disproportionate effect on the results of a t-test between the two sets.

PLS analysis, an extended multiple linear regression technique also known in the art, can also be used to determine, again between any pair of sample sets, which samples are most 'unlike' their supposed cohorts. This method differs from PCA in that in PLS, samples 'unlike' their cohorts are defined as samples affecting the expression profile difference between the two sample sets rather than mere strict difference from within-set cohorts which may or may not have an effect on comparative gene expression.

Upon the discovery of additional clinical parameters that consistently contribute to altered large-scale gene expression behavior, these newly identified parameters can be incorporated into new tree sort orders to generate more accurate sample sets as described in this embodiment to create new gene analysis contexts.

Once a hierarchical b-tree has been constructed and pruned of invalid samples (whether by physical chip parameter outlier analysis or biological outlier analysis, as discussed above) and sample sets (for sets containing too few samples for statistically rigorous results), analysis can begin. The system begins at the root node of the b-tree and runs a depth-first search, as illustrated in FIG. 1.

Another layer of complexity must be added to the b-tree analysis to attack the underlying biology inherent in this kind of sample organization. For each set of leaf nodes, one of two types of comparisons is useful and which comparison to select depends upon the attributes used in the b-tree sort order. For the normal versus disease state example given above (using a tree with sort order 'tissue/disease/morphology') the "normal" sample set is selected as a control and compared one at a time against each disease state (here, designated as the "experimental sample set"). This is termed a 1×1 comparison because a single leaf node is being compared against another single leaf node.

Alternative paths of analyses involve comparing a group of samples that share a particular attribute with all other samples but do not share that attribute. This can be termed a 1×N comparison. As an example, one can examine medication effects by comparing ACE (angiotensin converting enzyme) inhibitor-treated cardiac samples from patients against similar tissue from patients not undergoing ACE inhibitor treatment (regardless of other treatments). Visually this can be represented in the tree by selecting the leaf node for ACE inhibitor-treated cardiac tissue as the experimental group and combining all other morphologically normal cardiac leaf nodes as the control group for a 2-level deep tree defined as 'tissue/medication'.

A third type of comparison within the method of the present invention is also possible and can be referred to as an "N×N comparison". An N×N comparison would involve taking all leaf nodes that share more than one attribute and comparing them against all leaf nodes that share the opposite of those attributes, producing control and experimental sample sets that both incorporate more than one individual leaf node.

These arbitrary leaf node groupings are defined by a simple search grammar implemented to compare attributes either based on text strings (for descriptive attributes) or bucketed numeric values (for numeric attributes, e.g., patient age or cholesterol level). The search grammar consists of an array of references to sub-arrays, a maximum of one sub-array per level of the b-tree (and an implied minimum of no sub-arrays, which would return the entire body of samples). Each sub-array can contain one or more search terms (all of which are logically AND'd together). This array of arrays then acts like a filter, selecting which paths through the b-tree are valid in the current search context.

For example, in a tree built using a search order defined as 'tissue/secondary patient diagnosis' the term

[[T-62000],[DE-38010]]

specifies the branch containing all liver samples (T-62000 is the SNOMED code for liver) and the sub-branch containing liver samples from patients with hepatitis (DE-38010, the SNOMED code for hepatitis). This forms the experimental set. The control set, namely all liver samples from patients not infected with hepatitis, would be queried using

[[T-62000],[~DE-38010]].

The grammar defines a tilde ('~') as the negation operator. Thus, the above operation collects all liver samples that come from patients that are not infected with hepatitis. The samples returned by this statement then form the control set.

For each gene in the analysis (usually on the order of 40,000+ gene fragments in the case of the Affymetrix HG-U133 GeneChip® array) the average difference values are retrieved for each sample in each set. Sample set means, medians and variances are then calculated.

The pair-wise comparison method used by this system is efficient and modular. A two-tailed t-test is performed on the means and variances of the control and experimental sample sets to determine the statistical significance of the separation between the two sample sets. The null hypothesis used for the t-test is that the population means for the logs of the expression values are the same in the two sample sets. The alternative hypothesis is that the means are different.

Fold change is calculated on a per-gene basis, i.e., the fold change algorithm is applied to each gene separately for each comparison. However, in order to perform a t-test, both sample sets must have more than one sample regardless of whether a fold change can be reported.

The result of the t-test is screened at an alpha value ranging from 0.05 to 0.001 and all genes meeting the selected criterion are output to a result table along with supporting statistical data. Alternative statistical methods may be used to determine significance of sample set mean separation since the system was designed to remain modular and statistically method-agnostic.

The hierarchical method for organizing biological samples for analysis using a b-tree and a query grammar can be implemented in system memory or, alternatively, can be implemented on a disk file and searched using b-tree file searching algorithms found in modern database design and implementation practices.

The current invention allows for AND'ing together search terms in the grammar, that is, one can create groups based on samples that are not one thing AND not another. It will be appreciated that this grammar can be extended to allow for a logical "OR" operator, e.g., group samples that are one thing OR another.

It should also be noted that the b-tree mentioned in the current invention can be extended and populated with genes instead of samples, building a tree to refine gene sets based on shared attributes (such as gene ontology, cross-species homology, functional domains, etc.). Combining selected leaf nodes from a sorted gene tree with selected leaf nodes from sorted sample trees provides for a fine-grained control over analysis results (e.g., display all G-protein coupled receptors up- or down-regulated in any cancerous tissue).

In data creation and analysis applications where the expression metrics of more than one gene or gene fragment is/are being measured and studied, it may be desirable to examine the behavior of such subjects with respect to large scale biological applications. Such examples of multiple gene sets include members of gene or protein families such as G-protein coupled receptors (GPCRs), nuclear hormone receptors (NHRs) and protein kinases. Additional gene sets could encompass genes related by a biological process or pathway such as cell signaling transduction pathways, cell receptor-mediated secretory processes, apoptosis and cell death, cell division, etc. and other gene families and assemblies known to those in the art.

It is also conceivable that gene expression patterns for all genes within an organism could be created and compared to discover new relationships between genes based on functional genomics. One application could be for the categorization of unknown and unannotated genes and ESTs exhibiting behavior similar to that of well-characterized genes.

Furthermore, the present invention can be used to analyze data in a more traditional sample set-centric approach. Selecting a single control and experimental set of interest from a populated b-tree and iterating analyses for every gene across this single comparison would provide a global view of gene expression activity within a particular disease state or other biological context based on b-tree sort order.

In one embodiment, the gene expression results obtained from comprehensive b-tree comparisons for each gene or gene fragment are summarized in a matrix using a trinary, or similar, encoding scheme where up- and down-regulation of gene expression in the experimental (e.g. diseased tissue) state versus the control (e.g. normal tissue), would result in the assignment of 1 and −1, respectively, to the location i,j, where i represents the row in the matrix for a particular gene or gene fragment and j represents the column in the matrix for a particular pair-wise comparison (e.g. normal liver vs. liver cancer, etc). Thus, fold change values of the gene expression are not compared; rather, the qualitative aspect of the gene regulation is used as the encoding scheme and as the basis for comparison.

It follows that a value of "0" would then be applied to i,j locations where no gene expression regulation was observed for the $i^{th}$ gene or EST within the $j^{th}$ comparison. One can envision the application of this encoding scheme across the b-tree comparison space for each gene or gene fragment contained on a GeneChip® microarray or similar microarray.

This matrix can then be bi-directionally clustered to group together genes or gene fragments (or disease states) that are behaving in a similar manner across multiple related and divergent human diseases and clinical contexts within a gene expression database. This well-known technique is useful for learning the structure of a dataset without making any preconceived assumptions about said structure.

The length of the bit string generated per gene would be equal to the number of comparisons gathered from the b-tree (whose size, in turn, depends on the variety and depth of samples retrieved from the initial data source). Pattern searching algorithms can be applied to the clustered matrix to discover genes and gene fragments that exhibit predictably similar or, also just as interesting, predictably opposing gene expression regulation patterns in multiple experimental states.

FIG. 4 provides an example of the trinary (three-state) encoding scheme for downstream clustering of gene regulations derived from the algorithmic b-tree analysis. In FIG. 4a, exemplary output from the b-tree analysis algorithm is shown arranged in tabular form. This is the initial data from which the trinary encoding scheme will be derived. Entries of the form $G_x$ represent probe sets on a microarray, e.g., a GeneChip®, representing a particular gene. Table entries of the form $C_x$ indicate pair-wise comparisons, e.g., normal brain tissue compared to that of patients suffering from Alzheimer's disease. Numeric entries are for illustrative purposes only, and mean values are given in unitless "average difference" intensity values. FIG. 4b is a table showing the data from FIG. 4a encoded using the trinary encoding scheme. In an alternate embodiment, an Eisen-like color-coding scheme can be applied to this data table to facilitate analysis. For example, the +1 cells can be red and the −1 cells can be green. Clustering algorithms known in the art can be applied to cluster genes and disease states that share similar, or predictably dissimilar, expression profiles.

Figure 5:
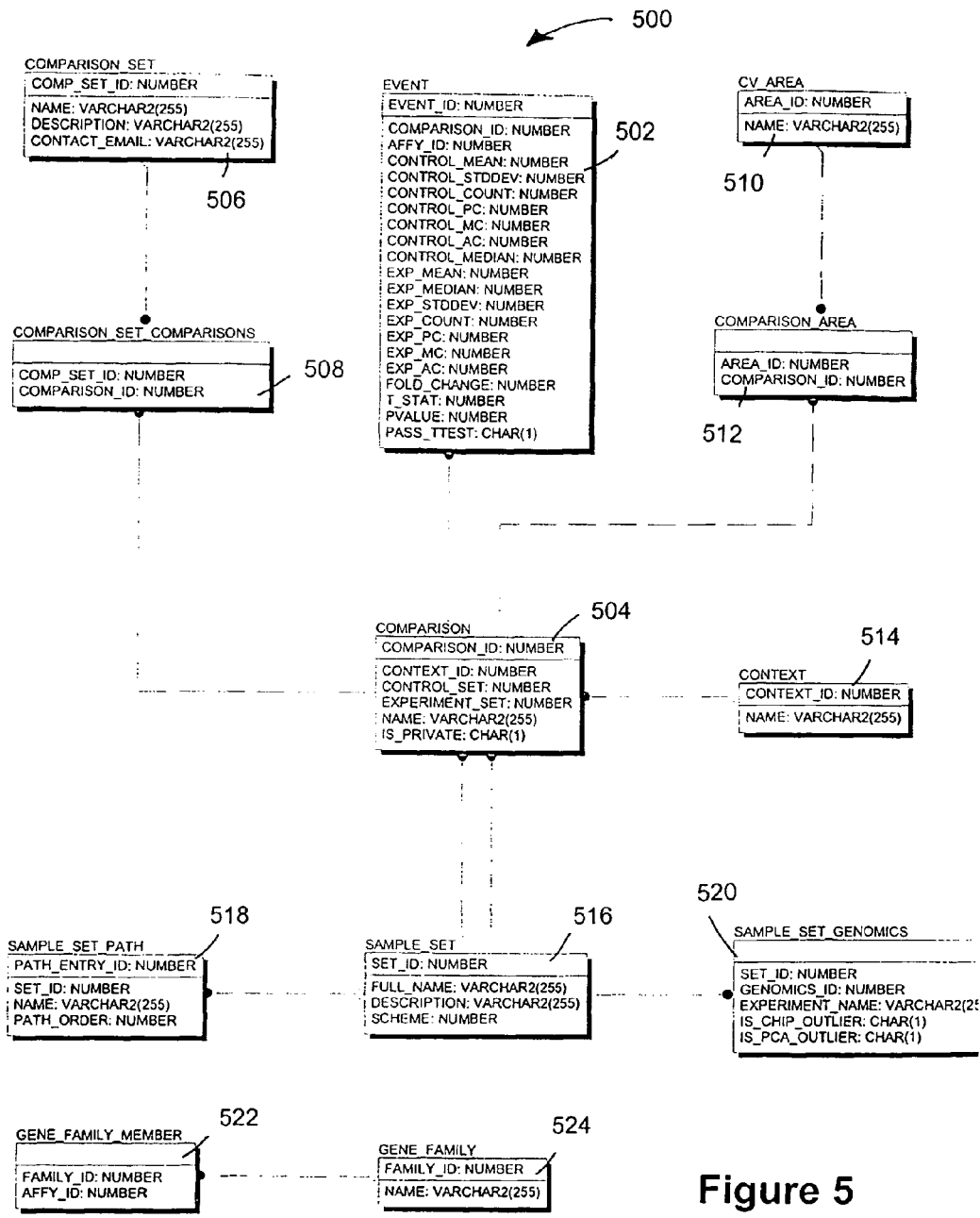
FIG. 5 is a data model for a relational database of gene regulation events.

In an alternate embodiment, the gene expression results obtained from comprehensive b-tree comparisons for each gene or gene fragment are summarized in a group of relational tables within a relational database 500, as shown in the data model of FIG. 5. Each block in the diagram represents a relational table, with the relationships between the tables indicated by dashed lines between the tables.

"Event" table 502 contains the results of regulation events, identification information for each control and experimental sample, results of the comparison of the control and experimental sample sets, e.g., fold change analysis, t-test, etc., and identifiers for each comparison. The primary key for Event table 502 is a unique identifier for each regulation event: EVENT_ID: NUMBER.

The table designated "CV_Area" 510 contains control vocabulary which may be used to narrow the area in which an analysis is conducted. For example, a search can be limited to information relating to the central nervous system or cardiovascular system. The primary key in this table is an AREA_ID: NUMBER that is associated with the name of the different possible areas of interest.

The "Comparison" table 504 contains records to describe the nature of the comparison and includes two foreign keys for identification of the control sample set and experiment sample set. The primary key in this table is the "COMPARISON_ID: NUMBER", a unique identifier assigned to each comparison between a control sample and an experimental sample. CONTEXT_ID: NUMBER corresponds to "Context" table 514, which provides a description of how the b-tree that produced the comparison result was organized. For example, referring to the example of FIG. 1, the b-tree sorts the sample set based on organ, disease, and morphology, respectively.

The 'Comparison_Area" table 512 is a joined table which links area information from table 510 with comparison information contained in table 504. "Comparison_Set" table 506 contains information for comparison data corresponding to pre-constructed sample sets that were generated independently of the b-tree analysis. Typically, such sample sets possess some error which prevents automated analysis, for example, incorrect indexing. Such sample sets are annotated manually by investigators whose contact information is provided in the table along with brief descriptions of the sample set(s). The primary key, COMP_SET_ID: NUMBER, provides a unique identifier to the pre-constructed sample sets.

"Comparison_Set_Comparisons table 508 is a joined table combining the identifiers for the automatically-generated comparisons from b-tree analysis, from table 504, and manually-generated comparisons from table 506.

"Sample_Set_Path" table 518 contains records of the pathway that was followed to navigate the b-tree to arrive at the leaf node which corresponds to the sample set. The primary key in this table is the PATH_ENTRY_ID: NUMBER.

"Sample_Set" table 516 contains records of the names and descriptions of the final sample sets generated by b-tree analysis. The primary key is SET_ID: NUMBER, a unique number assigned to each sample set.

"Sample_Set_Genomics" table 520 is a joined table linking the unique set identifier with a series of genomics menus and quality control information for each sample and each chip.

"Gene_Family" table 524 provides information about the gene family within which a probe set on Affymetrix GeneChip® microarray might fall, including the gene family name. For example, there are approximately 500 probes on the Affymetrix® HG-U133 chipset that qualify as GPCRs, so Gene_Family table 524 would have an entry for GPCRs. The primary key for this table is the FAMILY_ID: NUMBER.

"Gene_Family_Member" table 522 is a joined table linking the FAMILY_ID: NUMBER from table 524 with the identifier assigned to each gene or gene fragment according to the Affymetrix® identification system, e.g., probe set numbers and chip identification number. The AFFY_ID:NUMBER is recorded in Event table 502. For the example cited in the preceding paragraph, "Gene_Family_Member" table 522 would have approximately 500 entries, each with foreign key, AFFY_ID, pointing to a table in the database that defines the AFFY_FRAGMENT object. This organization is helpful for parsing events into gene-family specific groupings, for example, to find all GPCRs that are regulated in kidney cancer.

The relational database can be used to rapidly access and compare gene expression data generated for every gene or gene fragment on one or more GeneChip® microarrays, or other types of microarrays, thus providing for analysis are very large volumes of data to identify patterns and interrelationships between, e.g, diseases, treatments, etc. It may be appropriate to compare gene expression data for every fragment in a microarray with that of every other fragment on the same microarray. The resulting comparison data can be clustered according to any of a number of desired parameters, for example, normal versus disease, organ type, demographics, etc., then printed out in a report form. The database, which will be quite large, should preferably be refreshed on a regular basis in order to include new comparisons that become available as a result of ongoing research, thus expanding the possibility of identifying new patterns between gene regulation and diseases, organs, treatments, etc.

Figure 2:
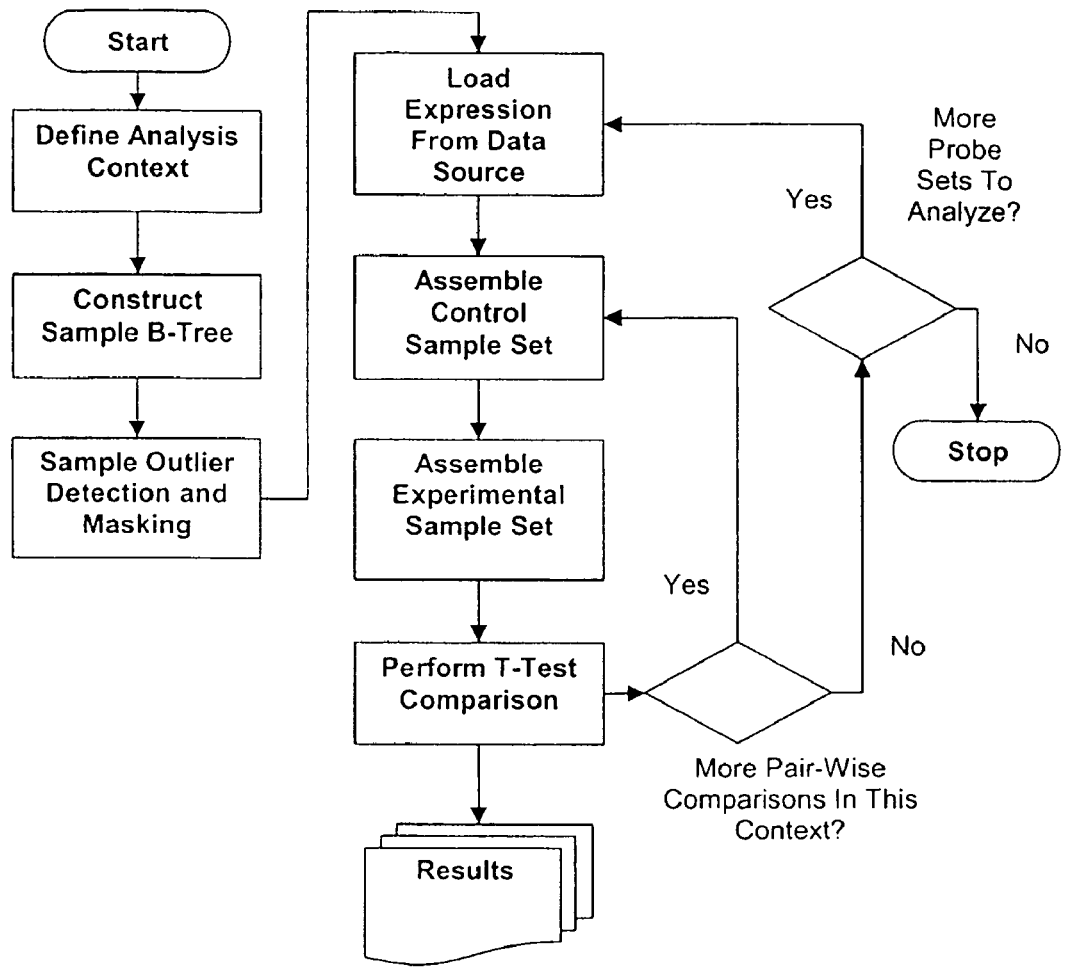
FIG. 2 provides a flow chart demonstrating the steps in the analysis process.
Figure 6:
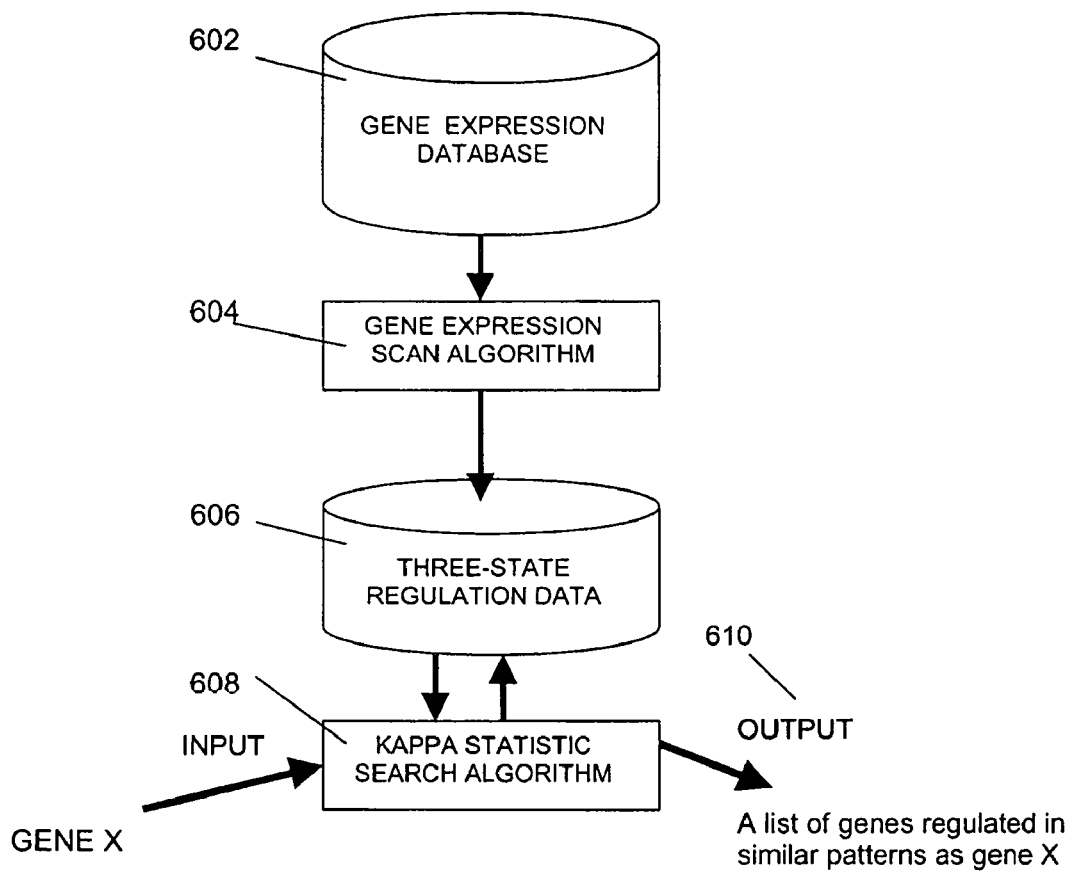
FIG. 6 is a flow diagram showing the analysis path for a three-state encoding scheme.

FIG. 6 illustrates an embodiment of the invention in which the three-state encoding scheme is used in conjunction with a statistical comparison method that provides a measure of similarity between any two probe sets. The gene expression database 602 and the gene expression scan algorithm 604 based on the hierarchical b-tree analysis have been previously described. (Gene expression scan algorithm 604 is shown in the flowchart of FIG. 2.) Following encoding of the data according to the three-state scheme, database 606 is created and stored. In the preferred embodiment, because these values can be reused, the three-state encoding of the entire gene expression database 602 is performed in advance of any search query then stored in database 606. Upon input of a search query for a gene or gene fragment of interest (designated here as "Gene X"), algorithm 608, which in the preferred embodiment is the kappa statistic, searches the trinary-encoded regulation data in database 606 to determine the level of similarity in gene regulation profiles relative to Gene X, generating output 610 in the form of a list of genes which are regulated in patterns similar to those observed for the gene or gene fragment of interest.

In a preferred embodiment, gene expression database 602 is a comprehensive collection of normal and diseased gene expression data. The sources of data in database 602 can be proprietary sources or publicly-available databases which may be used for data mining by pharmaceutical, biotechnology and other researchers and clinicians. The expression regulation behavior is aggregated into discrete three-state values (+1, −1 and 0) based on the direction of fold change values in normal versus disease comparisons.

For example, if Gene X is up-regulated 3.1 fold in breast cancer and has a t-test p-value<0.05, the assigned value for Gene X in a database for breast cancer would be +1. If the same gene is down-regulated with a fold change of −2.5 in liver cancer and has a t-test p-value<0.05, it would be entered in the database for liver cancer as −1. For each gene in database 602 there will be stored a corresponding three-state vector of length N representing that gene's regulation pattern in the N tissue/disease state combinations available in the database.

The kappa statistic (J. Cohen, 1960, "A Coefficient for Agreement of Nominal Scales", *Educational & Psychological Measurement* 20:p 37-46.) is a method of quantifying the level of agreement between two vectors of values. It enables the comparison of observed agreement versus agreement expected merely by chance. The agreement is quantified as an "agreement distance score" which is between zero, when agreement is no better than chance, and one, when there is perfect agreement. The formula for the kappa statistic (κ) is as follows:

$$\kappa = \frac{p_o - p_e}{1 - p_e}$$

where $p_o$ is the probability of observed occurrence and $p_e$ is the probability of expected or chance agreement. The standard error of the kappa statistic is given by $$se(\kappa) = \frac{1}{(1-p_e)\sqrt{N}}\left[p_o - p_e^2 - \sum_{i=1,N} p_{io}p_{oi}(p_{io}+p_{oi})\right]^{1/2}$$

where $p_{io}$ is the row total and $p_{oi}$ is the column total for a matrix containing the observed values (vectors). The Z score (the measure of statistical significance) is (κ/se(κ)).

Other commonly used measures which may be used as alternatives to the kappa statistic for finding a distance score include % agreement, Pearson correlation, Spearman rank correlation, Kendall's concordance, and others.

For a given gene, its regulation vector is retrieved from the data source described above and compared, using the kappa statistic, to measure the distance between the gene and every other gene in the data source. A list of high scoring genes is then generated.

In an alternate embodiment, other distance metric calculations can be employed in place of the kappa statistic. For example, score systems based on raw correlation coefficients, Euclidean distance, a BLAST®-type substitution matrix, etc. can be used.

In a preferred embodiment, a NCBI (National Center for Biotechnology Information BLAST®-styled input and output format is used to present co-regulation results. BLASTS (Basic Local Alignment Search Tool) is a well known set of similarity search programs designed to explore all of the available protein and DNA sequence databases. BLASTS uses a heuristic algorithm which seeks local as opposed to global alignments and is therefore able to detect relationships among sequences which share only isolated regions of similarity. The BLAST®-styled format allows a user to query the data stored in the data source, e.g., from a chip-wide scan, in a piecemeal fashion, retrieving a list of co-regulated genes with the statistics described above. The BLAST®-styled presentation is readily understood and interpreted by the research community at large, particularly when compared to the dendograms and complex tree-based visualization used with many existing programs. The BLAST®-styled output table lists the top ranked hits for similarity (distance score, in order of increasing distance) based on the kappa statistic and includes information such as Affymetrix probe set ID, Genbank ID, gene name, the values obtained from kappa statistic analysis and the alignments, i.e., the vector length N for the different pairs of three-state values corresponding to the N tissue/disease state combinations available in the database.

The algorithm for searching and extracting three-state encoded data, performing the pairwise similarity evaluation using the kappa statistic and generating the BLAST®-styled output was implemented using a Perl-based routine. As will be apparent to those of skill in the art, other programming languages and software may be used. For example, the statistical package available from SPSS, Inc. can be used for performing the kappa statistical analysis and generating the various values of interest. Similar statistical software is available from SAS Institute, Inc.

The three-state encoding of gene regulation data according to the present invention provides a new way to view expression data when compared with existing methods. The three-state values represent regulation directionality and are more logical from a biological standpoint. In contrast, two-state (Boolean) values are based on whether a gene is present or not, or whether the gene is regulated or not, without regard to directionality. Existing continuous analysis approaches use average mean expression values which can contribute a significant amount of noise to downstream clustering attempts. The three-state values of the present invention augment the ability to determine consistent gene behavior across states. For example, if two genes are primarily +1,−1 or −1,+1, then an instance in which they are +1,+1 can be considered a negative result. Boolean techniques, on the other hand, would be unable to identify such a detail.

The three-state method of the present invention provides a novel way to gather qualitative conclusions from expression data based on qualitative methods using discretized data as opposed to traditional, purely quantitative approaches. In a preferred embodiment, using a b-tree analysis as described above, biological data corresponding to a large number of biological samples can be pre-formatted into sample nodes in a node database for producing rapid responses to searches based upon pathological or biological parameters. In the preferred embodiment described herein, the system and method are used for knowledge extraction from a large database of gene expression data and data corresponding thereto. However, as will be apparent to those of skill in the art, data derived from measurement of other biological parameters can be the subject of a system and method according to the prevent invention. Examples of other such data are protein expression data (proteomic analysis), metabolite measurement (metabonomic analysis) as well as data resulting from the assay of other clinically and biologically relevant biomolecules. Generically, for purposes of this disclosure, a biological molecule, whether gene, protein, metabolite, amino acid, DNA, RNA, peptide, lipid, carbohydrate, or other biomolecule known to those in the art, will be referred to as a "biological material".

Gene expression values are pre-computed for each sample set; raw expression data for each of the individual samples within a set are not included in the sample sets. The "pre-formatting" of data is accomplished by organizing the data into granular sample nodes consisting of curated data sets that are categorized with respect to relevant pathological and biological considerations and summary gene expression values. Relevant statistics may be included in each sample set. In some cases, comparisons between sample nodes can be pre-computed and stored in the node database. It should be pointed out that the terms "sample set" and "sample node" are used interchangeably. Both terms refer to a curated collection of data through which runs a common thread for all samples that make up the set/node.

The node database can be used as a staging area to document and inventory existing curated sample sets and new curated sample sets as they become available. Also included in the node database are sample set nomenclature for identifying the data sets and data therein, summary data about the sample sets, and an explanation of how and/or why a specific sample set was created. Curation of the sample data sets may be achieved via a b-tree analysis in which quality control filters are applied to exclude outlier or other unreliable data, as described above. The b-tree analysis is used to organize clinically-related samples into leaf, or sample, nodes. Other sample sets may be manually curated by a pathologist or other expert in the field. The manually curated samples will be inserted into an appropriate, clinically-logical location within the b-tree structure and may be accessed in a similar manner to those nodes that were computationally identified during construction of the b-tree. One example of a situation that may call for manual curation is a tumor type that may exist in two types of tissue. Another example of a situation calling for manual curation is one in which the sample involves a number of subtle histopathology metrics.

In the preferred embodiment, the following gene expression values are pre-computed and stored in the database for each gene in each sample node, where n is the total number of samples in the sample set that makes up the node. These data can be extracted for reporting to the user in response to a gene specific query as well as for pre-computed comparisons and "on the fly" analysis:

Mean (average) intensity value with respect to n samples in that node.

Median intensity value with respect to n samples in that node.

Standard deviation of the mean intensity value.

$25^{th}$ and $75^{th}$ percent quartiles.

95% confidence intervals.

Present calls in sample node.

Marginal calls in sample node.

Absent calls in sample node.

Number of samples in a sample node: n

The number of present, marginal and absent call with respect to the n samples in the sample set can be used to calculate % present, marginal and absent calls on the fly. These pre-computed summary data can be used to produce automated reports for user selected genes, gene families and pathways and to generate the following types of calculations and data displays: Differential expression ("Diff X"), expression matching ("Match X", "Marker X" and "Normal X"), E-Northerns, sample set comparisons (by using the mean and standard deviation numbers to calculate the fold change and provide t-statistic and p values by performing pair-wise comparisons for gene reports and disease reports); and summary fragment data, i.e., gene detail, for a gene of interest.

In the exemplary embodiment, the node database includes the following content in terms of the fragments and Affymetrix GeneChip® microarrays:

Human: HG-U133 A and B chipsets (44,000 co-clustered sequences);

Rat: Ru34 A, B and C chipsets;

Mouse: Mu74 A, B and C chipsets.

After the data are arranged into the relevant sample sets, each sample set is assigned a set of attributes which can be used to facilitate organization for display and navigation by the user. Each set of attributes has a subset of categories into which data may be organized. Each sample set is assigned multiple attributes, which allows the user to configure his or her search on the most basic parameters of the key taxonomies on which the inventive system is based. In the preferred embodiment, three key taxonomies designations are identified: tissue, disease and medication. Because it is convenient and logical, this organization may be used to not only locate the desired sample set, but also to see what other related sets surround that sample set for comparative analysis, for example, to evaluate the information in a different context.

The following Table 1 provides an exemplary list of attribute classes that may be used for sample set organization:

TABLE 1

| Attribute | Exemplary Subsets |
|---|---|
| Sample Set ID# | Numeric ID# |
| Therapeutic Area | Cardiovascular, Oncology |
| Disease | Cardiomyopathy, atherosclerosis, normal, etc. |
| Organ System | Respiratory, Digestive, Female reproductive, etc. |
| Tissue | Heart, Ovary, Prostate, etc. |
| Parent | Yes with ID# of parent sample set or null |
| Medication | Digoxin, COX-2 inhibitor, aspirin, etc. or null |

Most of the attributes are self-explanatory and will be readily apparent to those in the art. The one possibly non-obvious attribute is the "Parent" attribute, which establishes relationships among sample sets that can be arranged into a hierarchical display to facilitate navigation and selection. To illustrate, a large sample set of tissues contains the potential for division into subsets corresponding to different tumor that may occur within a given tissue, or different stages of a tumor development. For example, a "Breast adenocarcinoma" set can be separated into four sets corresponding to four different stages of tumor. The adenocarcinoma set is deemed the "parent", while the four subsets are considered "children". Thus, the list of attributes for one of the child nodes would include a reference number identifying the parent sample set. It is also notable that 'normal' is not considered a separate attribute, but is included as a category of disease attribute, which is nevertheless consistent with the concept of the b-tree as described previously.

Existing sample nodes are periodically updated to include new data, and new sample nodes may be created based upon newly identified relationships between existing and/or new data. The new sample nodes may be automatically or manually created, as described above.

The sample nodes are classified in a logical format. In the preferred embodiment, the nodes are presented in order of increasing specificity, making it easy to sort through and select nodes for analysis and comparison. The following examples illustrate such organization:

Example 1

Human Breast Tissue

Normal

Infiltrating Ductal Carcinoma (all stages and receptor parameters)

Infiltrating Ductal Carcinoma Stage TIN0M (all receptor parameters)

Infiltrating Ductal Carcinoma Stage T1N+M (all receptor parameters.)

Etc.

Infiltrating Ductal Carcinoma ER+, PR+, Her2+(all stages)

Infiltrating Ductal Carcinoma ER+, PR+, Her2− (all stages)

Etc.

Infiltrating Ductal Carcinoma, Smoking (all stages & receptor parameters)

Infiltrating Ductal Carcinoma, Non-Smoking (all stages & receptor params.)

Etc.

Example 2

Human Kidney Tissue

Normal
Primary Malignancy, Clear Cell Carcinoma
Etc.
Secondary Malignancy from Liver Primary
Secondary Malignancy from Ovary Primary
Etc.

The sample nodes are selected to be as "granular" as possible as long as they make pathological and biological sense. The following is a exemplary, non-exhaustive list of the classes of sample nodes that can be generated.

1. Normal human, rat and mouse tissue morphology nodes.
2. All available human, rat and mouse-derived untreated cell lines.
3. All available human, rat and mouse-derived compound-treated cell lines.
4. Specific disease human, rat and mouse morphology nodes.
5. Grouped as a function of tissue, disease, morphology.
6. Grouped as a function of staged disease where applicable.
7. Grouped as a function of a basic disease-specific clinical parameter where appropriate, e.g., receptor status in breast cancer tissue.
8. Grouped as a parameter of primary tumor site w/respect to secondary malignancy.
9. Grouped as a function of another node-relevant "lifestyle" clinical parameter, e.g., smoking in breast cancer.
10. Medication-specific nodes for normal and if possible, disease morphology human samples.
11. Age-specific nodes for normal and disease morphology human samples, e.g., pre/peri/post menopausal for female human samples where appropriate.
12. Race-specific nodes for normal and disease morphology human samples where appropriate, e.g., heart (male and female), prostate (male), breast (female).

In the preferred embodiment, fixed computational filters are applied prior to loading comparison data into the node database. These filters were developed for use with expression data obtained using the GeneChip® HG-U133.

For each fragment that is compared between sample nodes, the % present call should exceed a pre-determined threshold. For example, for the Affymetrix U133A and B chips, this range is on the order of 50% for at least one of the two sample sets (nodes) involved in the comparison. A similar metric for rat and mouse chipsets will be on the order of 50-75%.

Additional computational filters can be automatically invoked when two nodes are compared. In one such filter, the system compares the means of the calculated sample set expression intensity for each fragment and calculates a fold change (using arithmetic means) value along with a statistical measurement of the fold change such as a p value or t-statistic. Only those gene expression regulation events that exceed 1.5 fold (up- or down-regulated) and have a p value$\leqq 0.05$ will be included.

Examples of other filters are:

a filter imposed where only nodes that have a sample ID number equal to or greater than a certain number will be available for analysis;

for each sample node, outlier analysis is performed to remove outliers with respect to inferior Affymetrix Gene-Chip® parameters (scale factor, % saturation, 5' and 3' ratios, etc) and biological parameters (if that sample significantly deviates from the median or average expression metrics for that group >3 sigma or standard deviations as determined by PCA). Under this scheme, the nodes can be trimmed and edited.

for each fragment that is compared between sample nodes, the mean intensity value must be at least 50 for either of the sample sets. This filter eliminates or reduces noisy regulated data.

As will be apparent to those of skill in the art, other filters can be applied automatically or as needed to remove outliers and/or unreliable data.

Each sample node is associated with the appropriate pathological and clinical parameters pertaining to that node. These parameters are also stored in the node database. The following is a list of information that is included for each node:

Node ID Number.

Node name and description title, which reflect species, tissue or cell type, and disease or compound treatment description.

Text that accurately describes the node with respect to pathological and clinically-relevant descriptions. Typically, the text will be written by a pathologist who is knowledgeable in the field.

At least one selected histopathology slide image from the node samples, one each high and low resolution.

Summary clinical parameter values for relevant disease nodes, e.g., PSA range for a human prostate adenocarcinoma node, with reference to normal (control) ranges. This information can be displayed in text, table or other graphical format.

Internet links, e.g., hyperlinks, to one or more outside information sources from which the user can gather additional information.

After the data are distributed into different sample nodes, comparisons can be performed on a pairwise basis for selected sample nodes. Certain comparisons can be pre-computed for nodes containing data which are likely to be frequently compared, as would be defined by relative locations in the b-tree organization. For example, differential expression in diseased tissue versus normal tissue for a given tissue would be a commonly-requested comparison, as would differential expression in diseased tissues corresponding to two different diseases of the same tissue. This pre-computed comparison data is also stored in the node database. In one embodiment, the comparison results can be stored in an N×N matrix where N is the number of nodes. However, since there are certain comparisons which do not make pathological sense, e.g., normal pancreas versus kidney small cell carcinoma, not all comparisons are needed, and an alternate storage scheme would be appropriate to conserve data storage capacity.

It should be noted that the frequently-compared pairings need not be pre-computed, but can be performed on-the-fly. If the pairwise comparisons are not pre-computed, the information for making the comparisons, e.g., the identities of the nodes to be compared, can be established in the node database. Whether or not pairwise comparisons between nodes are to be pre-computed depends on the available computing speed and the desired response. If the comparisons can be performed sufficiently quickly on the fly, it is not necessary to pre-compute the comparison, thus reducing the volume of data to be maintained in the database.

Additional pairwise comparisons can be performed in an on-the-fly basis. In particular, some pairwise comparisons might not fall within the b-tree organization logic, but pertain more to actual clinical knowledge. For example, it clinically makes sense to compare an oncology sample such as "Secondary malignancy of the ovary, primary site colon" to that of "normal colon" or "colon adenocarcinoma" since the actual ovary sample is from a colon tumor that has metastasized and traveled to the ovary, but is not composed of ovarian tissue per se.

The combination of sample nodes and pre-computed comparisons, if any, stored in the node database permits a system user to rapidly access data via a user interface which is organized in a logical format corresponding to the different node categories. In an exemplary embodiment, the selection of the search flow begins with the user selecting one of broadest categories from the user interface options of genes, gene families, sample sets and pathways.

Figure 7:
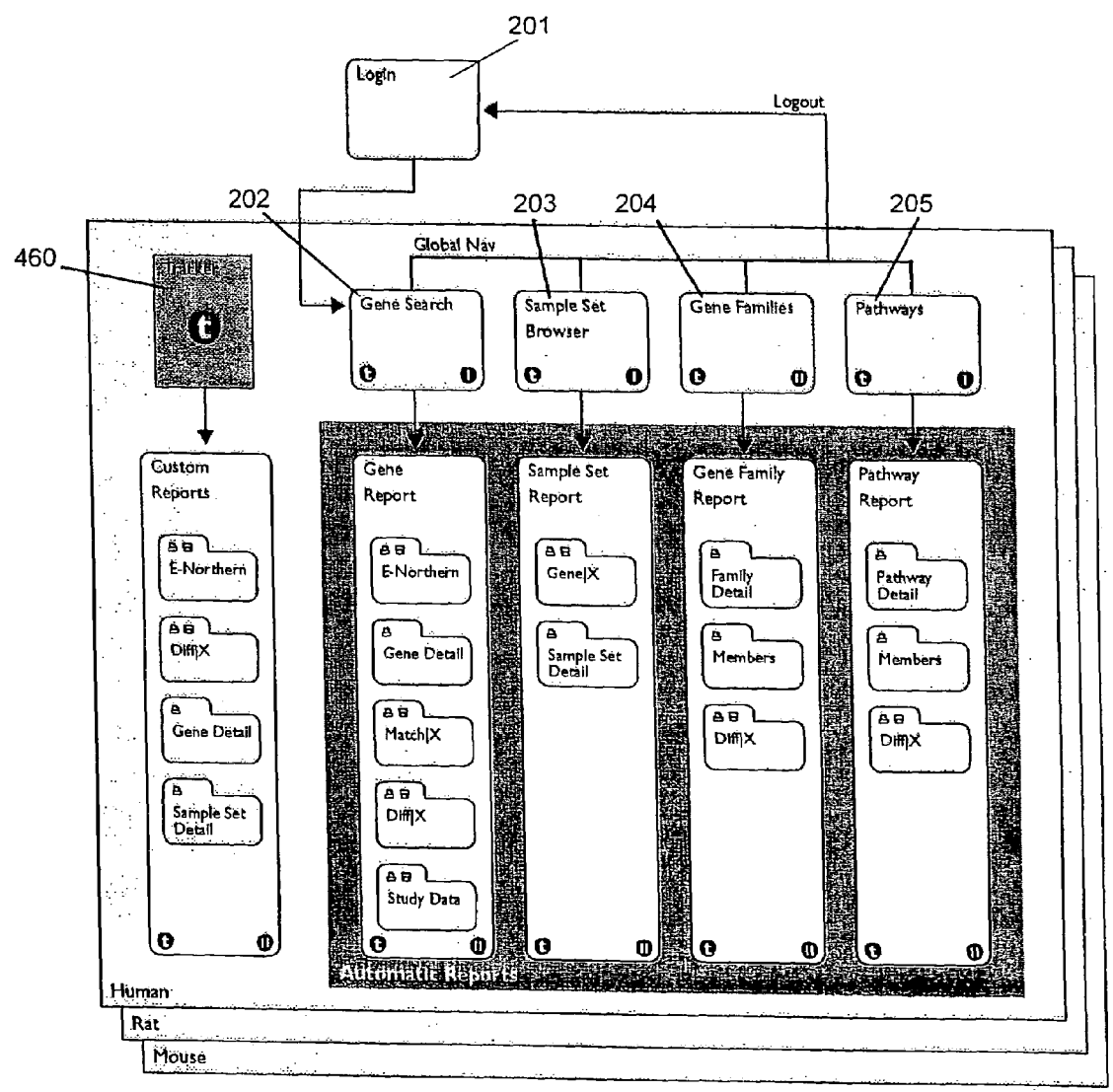
FIG. 7 is a user interface flow chart for implementing a set of Internet browsers for conducting rapid data mining in the database.
Figure 8:
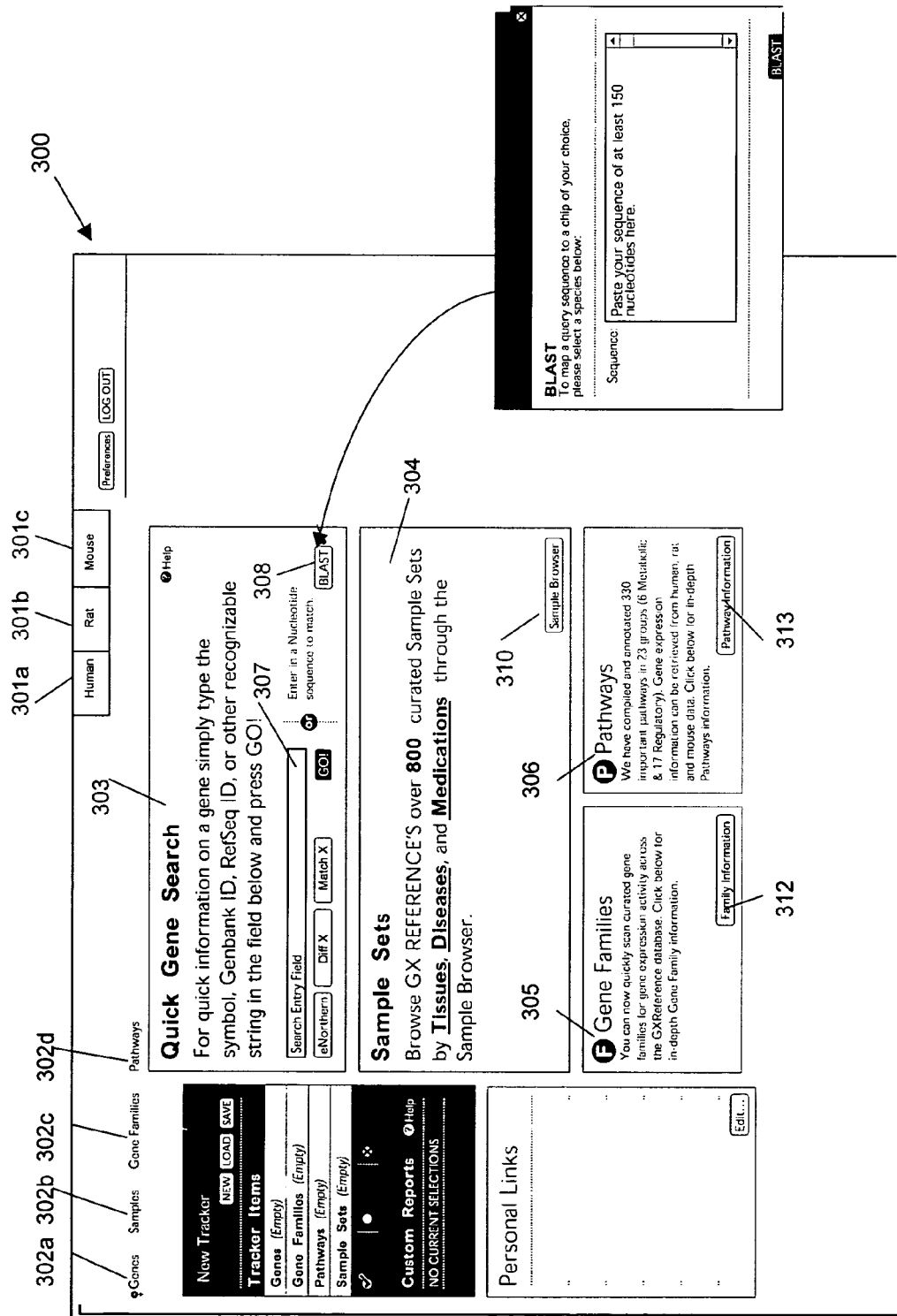
FIG. 8 is a graphical user interface (GUI) screen for accessing four different browsers for searching the database.

Referring to FIG. 7, the user interface ("UI") flow begins at the login/home page (201) through which the user obtains access and begins his or her research by selecting the type of search to be conducted. Because the database contains expression data for different organisms, e.g., human, rat and mouse, the user may need to select the organism of interest. In the exemplary embodiment, system is set to default to "human", such that if the researcher is interested in research on rat or mouse gene expression, it will be necessary to select the desired organism by clicking on the appropriate tab 301*a, b* or *c*, as shown in FIG. 8. From the login/home page 201, the user selects a content/query strategy selected from a plurality of categories. In the exemplary embodiment, there are four content/query strategies: "genes" 202, "sample sets" 203, "gene families" 204 and "pathways" 205, which may be selected on the graphical user interface (GUI) screen 300, shown in FIG. 8, by tabs 302*a, b, c* or *d*, respectively, or via links provided in boxes 303, 304, 305 or 306, respectively.

Figure 9:
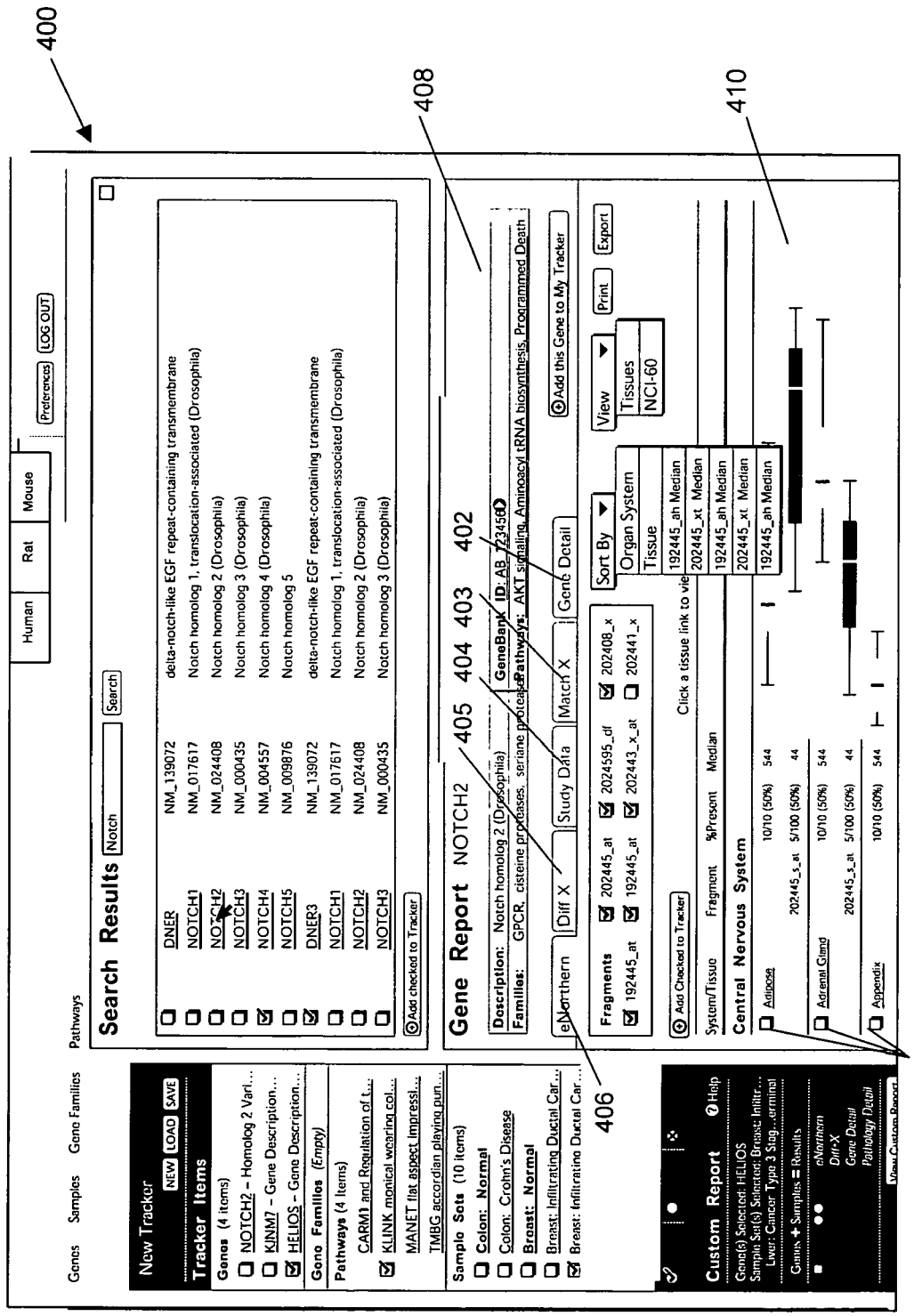
FIG. 9 illustrates an exemplary graphical user interface screen for the gene report page.

The user will be able to query the database on a selected gene of interest, i.e., a "query gene". If a gene search 202 is selected, the user has the option of entering the gene name, fragment name, public gene "token" ID, e.g., GenBank ID, RefSeq ID, UniGene, or other recognizable string into text box 307 within box 303. Alternatively, the user can select the link labeled "BLAST" (308) which presents a text box 309 into which a FASTA nucleotide sequence listing can be typed or pasted. The computer will then match the listed sequence with the appropriate fragment name, thus allowing the search engine to identify the appropriate gene expression data within the database. A gene report page GUI screen, an example of which is shown as FIG. 9, will then be displayed with the responsive data. The exemplary gene report page 400 provides the results following the user entry of a query for the term "Notch", offering the options of selecting a page displaying Gene Detail (tab 402) with detailed information about the selected gene, Match X (tab 403), Study Data (tab 404) with time series information, Diff X (tab 405), and E-Northern (tab 406), which is selected in the example and shown, in part, in the lower panel 410. The E-Northern results displayed in panel 410 include links 412 through which the user can select specific tissue types for display of summary expression data (from the corresponding sample node) or related data.

In addition to displaying information about the query gene, the gene can be automatically mapped to gene families and pathways by way of the panel 408. Information for performing the automated mapping, as well as providing for other automated data reports, can be stored in the node database using a sample set comparison scaffold generated at least in part according to the b-tree method.

In the case of HG-U133, the gene detail report can provide the summary data for all 44,000 co-clustered sequences (mRNA and ESTs), all of which are stored in the node database, in a list format. External links to Genbank and other public records may also be provided, as shown in panel 408. The different analyses can be selected via tabs or links displayed on the gene report page.

Selecting "Diff X" tab 405 on the gene report page provides a differential expression analysis which lists all statistically significant differential regulation events for the selected gene via the associated fragments. The comparisons are based on those established in the node database. As discussed previously, the comparisons may be either pre-computed, performed on-the-fly, or a combination thereof, using the pre-computed expression data stored in the node database for each sample set. Displayed information includes the gene fragment identifier, control set description, experimental set description, fold change and associated p-value. The set descriptions provide hyperlinks to the described sample set stored in the node database. The results may be rearranged according to the values of selected parameters or filtered to exclude data based on selected parametric ranges or values, e.g., on p-value. Further, the user can swap the pairwise comparison direction, e.g., from A versus B to B versus A, to change the fold change directionality.

By selecting the E-Northern tab 406 on the gene report page, an automated E-Northern analysis can be performed based on normal tissue sample sets in the node database. In the exemplary embodiment, a panel of normal human tissue sample sets is provided, as well as a panel of NCI 60 cell lines. Panels of normal tissue for rat, mouse, and/or other model organisms (strain specific) may also be provided. The E-Northern is displayed as a series of horizontal boxes and whisker plots that provide information about the mean and range of expression of a single fragment in a selected tissue. Summary statistics obtained from the pre-computed expression data for each sample set are used to generate the plots. One or more co-clustered fragments for each gene on the E-Northern can be displayed, sorted alphabetically by tissue, by organ system, or median expression value of each fragment shown on the E-Northern. Where there are multiples of a given sort parameter shown, e.g., organ systems or tissues, each is displayed in a separate box, with the boxes stacked or otherwise tiled for display. In the GUI screen that displays the E-Northern report for a selected fragment (or fragments), each listed tissue type provides a link to the sample report for the corresponding sample set in the node database.

Pattern matching is often powerful when examining gene expression behavior across panels of tissues. Such questions are particularly relevant in cases where a researcher may wish to elucidate the function of an unknown gene by comparing its expression profile to those of known genes. Expression profile pattern matching is also useful in target prioritization efforts, where the researcher may want to understand upstream or downstream regulatory networks that impact his or her primary drug target or, in some cases, when seeking alternative targets that may be easier to drug. Study of these coordinately regulated genes can lead to a better understanding how complex interrelated genetic networks behave in human disease, which may provide valuable information for the development of novel therapeutic approaches. The present invention provides for a number of different pattern matching analyses.

Selection of the "Match/X" tab 403 on the gene report page provides a listing of gene fragments corresponding to genes in the database that have significant expression regulation patterns with respect to the automated sample set most similar to the query gene. The resulting Match/X list contains genes or gene fragments having the most similar patterns as well as those that have inverse (anti-nodal) patterns.

The Match/X algorithm uses the trinary (−1, 0, +1) encoding scheme discussed above to generate a matrix that can be used to determine a distance score between any two genes in the matrix. A 3×3 contingency table for the two genes is created for the two genes. Table 2 provides an example contingency table $C^{mn}$ for genes m and n represented by row vectors $T_m$ and $T_n$ with entries $c_{ij}^{mn}$ (i=−1, 0, 1; j −1, 0, 1)

TABLE 2

|  | $T_n = -1$ | $T_n = 0$ | $T_n = 1$ | Row Totals |
|---|---|---|---|---|
| $T_m = -1$ | $c_{-1,-1}$ | $c_{-1,0}$ | $c_{-1,1}$ | $c_{-1,.}$ |
| $T_m = 0$ | $c_{0,-1}$ | $c_{0,0}$ | $c_{0,1}$ | $c_{0,.}$ |
| $T_m = 1$ | $c_{1,1}$ | $c_{1,0}$ | $c_{1,1}$ | $c_{1,.}$ |
| Column Totals | $c_{.,1}$ | $c_{.,0}$ | $c_{.,0}$ | d |

The sum of the diagonal elements of $C^{mn}$ provides the observed agreement between $T_m$ and $T_n$:

$$O_{mn} = \sum_{k=-1}^{1} c_{kk}^{mn}.$$

The expected agreement between $T_m$ and $T_n$, under the null hypothesis that the genes are independent, is $$A_{mn} = \sum_{k=-1}^{1} c_{k.}^{mn} \cdot c_{.k}^{mn} \cdot \frac{1}{d}.$$

The kappa statistic for co-regulation is defined as $$\kappa_{mn} = \frac{O_{mn} - A_{mn}}{1 - A_{mn}},$$

where $\kappa_{mn}$ is 1 for perfect agreement and 0 (zero) for agreement less than chance. ($\kappa_{mn}$ is floored at 0 in such cases.)

The fact that some of the disease comparisons share a common normal comparison sample set means that some columns of the matrix are not strictly independent. However, the bias in κ introduced by this issue can be shown to be quite small in the context of the large sample sizes typically involved in gene expression data studies.

Also of interest are inverse co-regulation events. The observed inverse agreement between $T_m$ and $T_n$ is $$O_{mn}^* = \sum_{k=-1}^{1} c_{kk*}^{mn}$$

where k*=−k.

The expected inverse agreement between $T_m$ and $T_n$ is $$A_{mn}^* = \sum_{k=-1}^{1} c_{k.}^{mn} \cdot c_{.k*}^{mn} \cdot \frac{1}{d}.$$

The kappa for inverse co-regulation is defined as $$\kappa_{mn}^* = \frac{O_{mn}^* - A_{mn}^*}{1 - A_{mn}^*},$$

where $\kappa_{mn}^*$ is 1 for perfect agreement and 0 (zero) for agreement less than chance. As above, $\kappa_{mn}^*$ is floored at 0. The distance metric, also referred to as the "Match/X distance score", is then defined as $$X_{mn} = \min(1-\kappa_{mn}, 1-\kappa_{mn}^*).$$

Co-regulation or inverse regulation is denoted by:

$$r_{mn} = \begin{cases} +1 & \text{for } \kappa_{mn} > \kappa_{mn}^* \\ 0 & \text{for } \kappa_{mn} = \kappa_{mn}^* = 0 \\ -1 & \text{for } \kappa_{mn} < \kappa_{mn}^* \end{cases}.$$

When the genes are co-regulated, $r_{mn}=+1$, and when the genes are inversely regulated, $r_{mn}=-1$. When $r_{mn}=0$, neither co-regulation nor inverse regulation is present, and $X_{mn}$ will equal 1.

The large sample variance of $X_{mn}$, under the null hypothesis that the genes are independent, is $$\text{Var}(X_{mn} \mid r_{mn} = 1) = \frac{O_{mn}/d \cdot (1 + O_{mn}/d) - \frac{1}{d^3}\sum_{k=-1}^{1} c_{k.}c_{.k}(c_{k.} + c_{.k})}{d \cdot (1 - O_{mn}/d)^2}$$

$$\text{Var}(X_{mn} \mid r_{mn} = -1) = \frac{O_{mn}^*/d \cdot (1 + O_{mn}^*/d) - \frac{1}{d^3}\sum_{k=-1}^{1} c_{k*}.c_{.k*}(c_{k*.} + c_{.k*})}{d \cdot (1 - O_{mn}^*/d)^2}.$$

Thus, an approximate p-value can be calculated for $X_{mn}$ using $$Z = \frac{X_{mn}}{\text{Var}(X_{mn})^{-1/2}}.$$

Example 3 below provides an exemplary application of the Match X pattern matching algorithm which employs the kappa statistic to find a distance score.

For initial validation of the distance score, directionality and Z-score, the results can be compared for random versus co-clustered pairs of fragments. Co-clustered fragments are those that are represented by unique probe sets on the Gene-Chip® which map to the same human gene transcript. For random pairs of fragments, approximately 50% are expected to show no detectable co-regulation or inverse regulation, ~25% to show some level of co-regulation, and ~25% to show some level of inverse co-regulation. For those that show inverse or co-regulation, the degree of that relationship is expected to be relative small on the average. In contrast, for co-clustered fragments, up to 100% can be expected to show co-regulation at a detectable level, and the degree of that relationship to be more pronounced on average (lower distance scores) that for random pairs of fragments.

Figure 14:
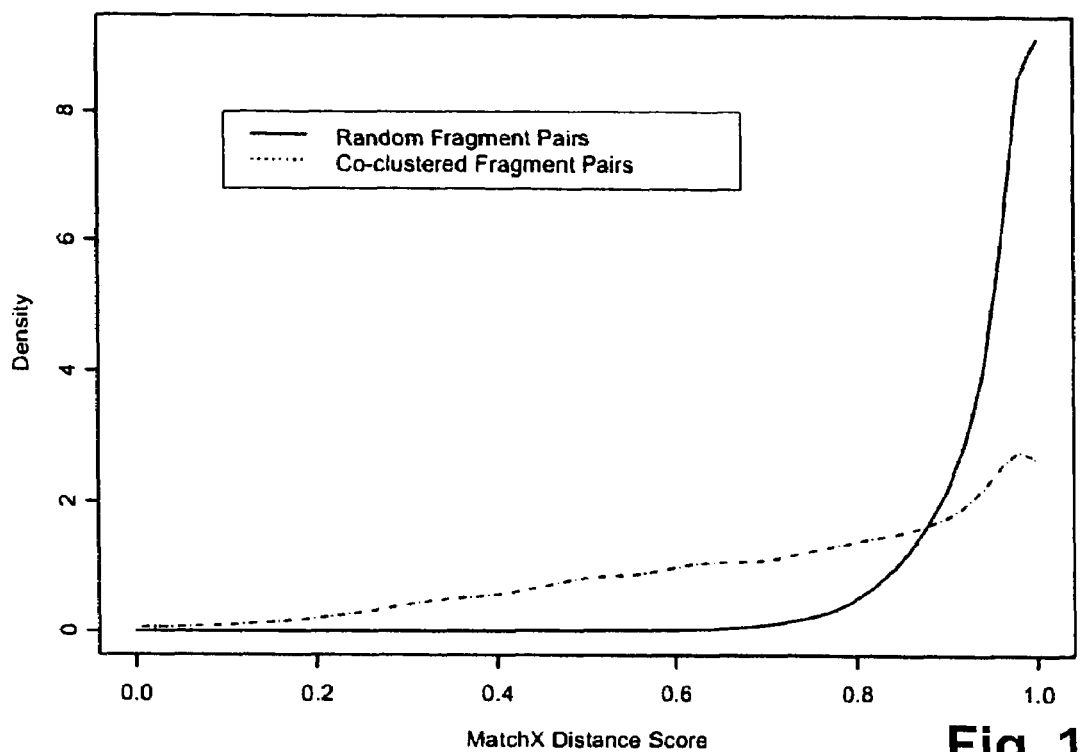
FIG. 14 is a plot showing the distribution of March/X distance scores.

FIG. 14 shows the distributions for random fragment pairs and co-clustered fragment pairs. Given 44,760 fragments, the number of distinct fragments on the Affymetrix Hu133A/B GeneChip® array set, there are ~1 billion unique pairs of fragments. FIG. 14 includes a random sample of 2 million of these pairs plus all 22,322 pairs of co-clustered fragments. The distribution of distance scores for the random pairs is heavily weighted towards large distances (mean=0.96, $25^{th}$ percentile=0.94, $75^{th}$ percentile=1.00). In contrast, the distribution of co-clustered pairs is shifted substantially towards smaller distance scores (mean=0.75, $25^{th}$ percentile=0.59, $75^{th}$ percentile=0.96.)

The directionality and significance level of the distance scores were also evaluated, with the results shown in Table 3.

TABLE 3

|  | Random Fragment Pairs | Co-clustered Fragment Pairs |
| --- | --- | --- |
| Co-regulation $r_{mn} = +1$ | 24.3% (6.0% sig) | 77.4% (62% sig) |
| No regulation pattern ($r_{mn} = 0$) | 53.6% | 20.8% |
| Inverse regulation ($r_{mn} = -1$) | 22.1% (4.1% sig) | 1.6% (0.1% sig) |

Significant scores were defined as those having Z-scores>5, corresponding to a two-sided p-value≦$0.05/44760 \approx 1\times 10^{-6}$. For the random fragment pairs, there is an approximate 25%/50%/25% breakdown with respect to directionality, with a slight enhancement of co-regulation over inverse regulation. Approximately 10% of the random pairs show a relationship above the level of chance. For the co-clustered fragments, approximately 77% show detectable co-regulation, while very few pairs show detectable inverse correlation. Additionally, the number of pairs with distance scores outside of the range of chance has increased to 62%. Overall, the comparison of random pairs of fragments to pairs of co-clustered fragments provides an initial statistical validation of the approach.

Figure 15:
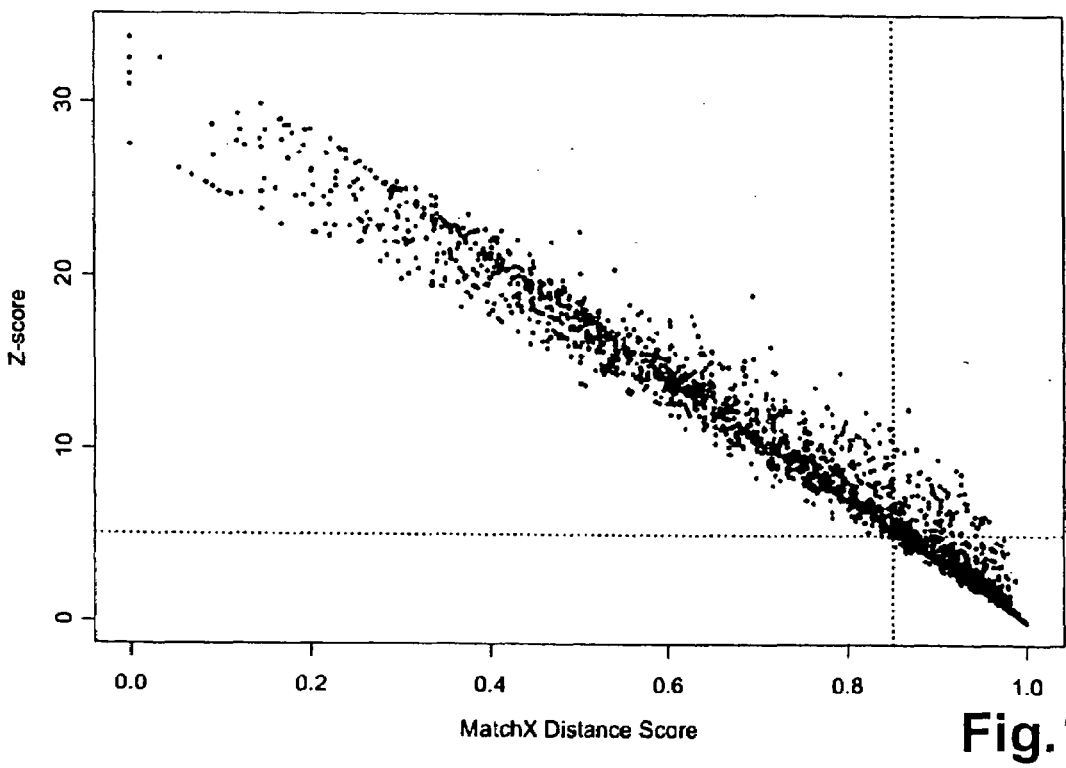
FIG. 15 is a plot showing the relationship between Z-score and Match/X distance for co-clustered fragments.

FIG. 15 shows the relationship between Z-score and Match/X distance for the co-clustered fragment pairs. The relationship within the random pairs is almost identical. These data indicate that there is a relatively tight relationship between Match/X distance and Z-score, and thus, for ease of interpretation, one can consider cutoffs based on the distance score. For example, a Z-score cutoff of 5 ($p<1\times 10^{-6}$) would correspond to a distance cutoff of $X_{mn}<0.85$ for determining gene relationships. In practice, however, a more stringent cutoff is preferred. A distance cutoff of $X_{mn}<0.5$ yields that highest quality, most interpretable results. This corresponds to a Z-score of 15. While results in the range 0.5 to 0.85 may still be statistically significant, the relationships tend to be relatively weak, with the significance driven by the large numbers of diseases available for analysis.

Additional analyses based on gene expression pattern matching can be made available for selection as part of the gene report by providing additional tabs (not shown in the Figures). A first additional analysis, referred to as "Marker/X" can be used to provide a listing of all genes that are uniquely expressed in a specific tissue of interest. The primary input is a specific tissue of interest, while the output is a listing of marker genes that are uniquely expressed within the specific tissue. Applications of marker gene discovery include the development of diagnostics and specifically targeted therapeutics. Understanding which genes are unique to specific tissues can provide insight into the molecular mechanisms of cellular growth and differentiation, including genetic programs of human development. Marker gene identification will also provide the basis to understand how regulation of these marker genes is perturbed during abnormal cellular growth and differentiation, such as in cancer. Global knowledge of the complete repertoire of marker genes that uniquely describe a specific tissue type may even enable scientists to genetically alter developmental programs in stem cells to create tissue and organ cultures for transplantation or other biomedical uses.

The "Marker/X" algorithm is executed by first generating mean expression values for each normal tissue set in the database. The mean values are transformed by adding twenty (20), then taking the log 2 (log base 2) to generate transformed means. For an input tissue, a weighted mean is computed using the transformed mean values, excluding the input tissue. Then, a weighted standard deviation is computed using the transformed mean values, excluding the input tissue. In the exemplary implementation, weights are 1 for non-CNS tissues and 0.2 for CNS tissues, however other weights may be used where appropriate. Next, a pseudo t-score is computed according to the relationship:

$$\frac{((\text{Mean of input tissue}) - (\text{Weighted mean of other tissues}))}{(\text{Weighted standard deviation of other tissues})}.$$

Note that as an alternative to the use of mean values, median values may be used in the above steps. The pseudo t-score is then used to rank the genes according to expression in the tissue of interest.

Marker/X is a robust and simple tool for elucidating information about tissue-specific gene markers in an intuitive and biologically meaningful context. Through the identification of marker genes, researchers will be able to advance their understanding of and potentially exploit the molecular basis of tissues uniqueness to develop novel therapeutics.

Another additional analysis option based on pattern matching is a variation on the Match/X analysis that, rather than global application, is focused on individual therapeutic areas. The "Local Match/X" algorithm is a gene expression pattern matching algorithm that can be used to identify genes having coordinate or inverse coordinate gene expression patterns when compared to a gene of interest. Similar to the above-described Match/X algorithm, the Local Match/X algorithm functions to identify coordinate or inverse coordinate gene expression patterns relative to a gene of interest, but performs the analysis using only subsets of tissues related to a specific therapeutic area. Examples of specific therapeutic areas include Central Nervous System, Cardiovascular System, Inflammation, Oncology, and Metabolism. The key difference from Match/X is that Local Match/X seeks to identify genes that are similarly regulated in a more restricted and focused context. The principal biological question addressed by this algorithm is to provide a listing of all genes that behave similarly to a gene of interest, across a limited panel of disease and normal tissues, restricted to a specific therapeutic area of interest. The primary input is a gene of interest and a selected therapeutic area to restrict the analysis to. The output is a list of genes that share coordinate or inverse coordinate gene expression patterns with the gene of interest across disease and normal tissues within the selected therapeutic area.

The Local Match/X algorithm can be applied for a therapeutic area using a set of N disease versus normal comparisons. For each comparison, a two-sample t-test is performed for each gene. The results of the t-test are coded as follows:

−1 if p-value<0.05,
   fold change disease: normal<0.67,
   % present in each disease or normal≧50%,
   mean in either disease or normal>50.
+1 if p value<0.05,
   fold-change disease/normal>1.5,
   % present in either disease or norm≧50%,
   mean in either disease or normal>50.
0 otherwise.

Within a therapeutic area, there is for each gene a vector of length N where the values are in the trinary coding scheme. The distance metric for any pair of genes is [1−kappa(gene1, gene2)] as described in the Match/X application. The net result for each input gene is a set of matched genes, organized by therapeutic area.

Still another gene expression pattern matching analytical method that can be selected by the user is the "Normal/X" algorithm, which functions to identify coordinate or inverse coordinate gene expression patterns relative to a gene of interest, but performs the analysis using only normal tissues. Although similar to the Match/X analysis, the key difference from Match/X is that Normal/X seeks to identify genes that are similarly regulated in a biological system that is theoretically normal and unperturbed. The principal biological question addressed by this algorithm is to provide a listing of all genes that behave similarly to a gene of interest across normal tissues. The primary input is a gene of interest. The output is a list of genes that share coordinate or inverse coordinate gene expression patterns with the gene of interest across normal tissues.

Typically, identification of genes with similar expression profiles is achieved by using a distance metric on sample level expression values. Examples of the distance metric include correlation, euclidean distance, etc. The differences between the Normal/X approach and such approaches are that the present method uses sample sets rather than samples as the input to the algorithm; and a weighted distance metric is used with weights varying by tissue type.

The described differences serve to avoid problems caused by uneven tissue or organ system representation in the database. For example, there may be several hundred breast samples in the database but only about ten adrenal gland samples. A sample centric approach would be driven almost entirely by the expression pattern in the breast samples. Further, there can be about 40 distinct tissue types within CNS, but only two within the endocrine system. The present method is designed to keep CNS from unduly driving the algorithm.

The Normal/X algorithm includes the steps of calculating the tissue set mean values for each gene, denoted by $M_{ij}$ where i indexes genes and j indexes tissues. Then, transform the mean values and calculate $N\# = \log 2(M_{ij}+20)$. The similarity metric for any two genes G1 and G2 is then the weighted correlation of $N_{G1i}$ and $N_{G1j}$ across all j, with weights $w_j$ assigned to each tissue. In the preferred embodiment, $w_j=1$ for non-CNS tissues and $w_j=0.2$ for CNS tissues. Other weights may be used as appropriate. The Normal/X distance metric is then 1 minus the absolute value of the Similarity Metric.

Another additional analysis that may be selected as part of the overall gene report includes time-series data showing gene expression levels for query genes as a function of experimental time and treatment. This analysis, which may be referred to as "Study Data", selected using tab 404, is displayed in the form of scatter plots of gene expression levels for one or more selected sample sets as they vary with time and/or treatment.

If the user wishes to conduct research according to gene families, he or she will select the content/query strategy "Gene Family" 204 by clicking on either tab 302c or link 312 in box 305. This generates a new GUI screen (not shown) for "Gene Families", which displays a menu or table with a listing of gene families. Using this data mining strategy, the user can generate comprehensive expression information as a function of gene family classes where each of the listed gene family names provides a link to information about the selected family as well as a listing of gene family members. Many of these classes constitute known druggable classes as constitute current drug and disease screening platforms in pharmaceuticals and biotech. Examples of gene families that can be included are G-protein coupled receptors (GPCRs), nuclear hormone receptors (NHRs), protein kinases (pkinases), serine proteases, cysteine proteases, matrix metalloproteinases, ion channels, chemokines and cytokines, CD surface antigens, gamma-carboxylases phosphodiesterases, protein phosphatases, cytochrome P-450 enzymes, and short chain dehydrogenases/reductases, etc. An additional special category of gene family can include the targets of the top 300-500 drugs.

The Gene Family GUI screen also provides links to relevant public information sources for the gene families so the user can obtain more information.

A summary gene expression report for each gene family can be automatically generated in, for example, table form. Such a table contains summary information of all of the gene families for which data is stored in the node database as a function of the regulation of their specific gene target members in various therapeutic areas. The system of the present invention also maps the gene family to the relevant biological pathways.

Referring back to FIG. 8, as a third alternative, the user can select a broad search strategy according to pathway by clicking on either tab 302d or link 313 in Pathways box 306, which takes the user to the Pathways GUI (not shown). Using this approach, the user can conveniently query gene expression information for genes assigned to known defined biological pathways, e.g., MAP kinase, Apoptosis/Caspase pathways, etc. In an exemplary preferred embodiment, there are approximately 300 pathways available based upon Bio-Carta® and KEGG pathways.

A query under the "Pathways" approach can occur by selecting one of the pathway categories listed in a box or pull down menu in the Pathways GUI by pointing to and clicking on the name of the desired pathway. Similar links to external public databases are provided. In the exemplary embodiment, the Pathways GUI provides an intuitive, biologically-oriented process for pathway selection based on two high level groupings: "Metabolic" or "Regulatory". Under Metabolic pathways, the user can select links to one of several metabolic pathways as a function of biomolecule type including, but not limited to, lipid, amino acid, carbohydrate, co-factor and vitamin, energy and nucleotide. Under Regulatory pathways, the user is offered the option of classes corresponding to process; e.g., cellular processes, immunology, human diseases and gene information processing. Within each process class is a selection of one or more groups of pathways. These may then be further broken down into classes. For example, under "Cellular Processes", if the user selects "Signal Transduction", data is included in the exemplary node database for 47 possible pathway options. Non-limiting examples of the pathway options in this category are actions of nitric oxide in the heart, bioactive peptide induced signaling pathway, and CARM1 and regulation of the estrogen. Other options will depend on the data included in the database and will be apparent to those in the art. For convenience, the pathway options can be listed in alphabetical order or organized according to a clinically-logical criterion. Each of the listed pathways includes information regarding the number of genes in the pathway The fourth broad search option is the "Sample Set Browser" 203 (also referred to as the "Sample Browser"), which is initiated by selecting link 310 in box 304 of GUI screen 300 shown in FIG. 8. The Sample Set Browser represents that entire database of genetic samples in the node database organized into clinically relevant sample sets (nodes) according to one of three distinct taxonomies: Tissues, Diseases or Medications. Upon selection of link 310, the system displays Sample Set Browser screen 450, an example of which is provided in FIG. 10, which directs the user to first select a search type (pull-down menu 451), which offers the option of taxonomy, and then category (scrolling menu 452), a sub-category (scrolling menu 453) and specific sample set (table 454). (It should be noted that the display and selection format described with respect to the exemplary embodiment is not intended to be limiting. Other means for display and selection of the options will be readily apparent to those of skill in the art.)

The displayed contents of menus 452 and 453 and table 454 depend on the taxonomy selected by the user. If "Tissues" is selected from menu 451, menu 452 will contain a list of organ systems including cardiovascular, central nervous system, GI/Digestive, respiratory system, reproductive system, skeletal system, endocrine system, excretory system, skeletal system, and muscular system. If "Diseases" is selected from menu 451, menu 452 will list options corresponding to therapeutic areas such as oncology, inflammation, metabolic diseases, etc. If "Medications" is selected from menu 451, menu 452 will display a list of medications.

The displayed contents of menu 453 will depend on the selection made from menu 452. If Organ System is selected from menu 452, a list of the tissues in that organ system will be provided in menu 453. For example, for GI/digestive from menu 452, menu 453 will list options of stomach, colon, etc. If therapeutic area is selected from menu 452, a list of diseases relevant to the area will be provided in menu 453. For example, for oncology selected from menu 452, menu 453 will list options such as benign tumors, primary malignancy, secondary malignancy, etc. If medication is selected from menu 452, a list of the tissues for these sample sets with respect to the medication will be listed in menu 453.

As previously described, sample sets have associated attributes that allow the sort/classification criteria and system described above. After the user makes his or her selection from menu 453, the sample sets with the selected attributes are displayed in table 454. The specific sample sets listed in table 454 correspond to the sample nodes, which can be selected to open a sample report page.

Table 4 provides a summary of the sample set sort and classification options that can be initiated via GUI screen 450:

TABLE 4

| Step 1 | Step 2 | Step 3 | Step 4 |
|---|---|---|---|
| Tissues | Organ Systems | Tissue Type | Diseases |
| Diseases | Therapeutic Areas | Disease Type | Tissue |
| Medications | Medication | Tissue Type | Tissue |

The medications sort is a 2-level classification as a result of only normal tissue sets having a medication context.

Figure 10:
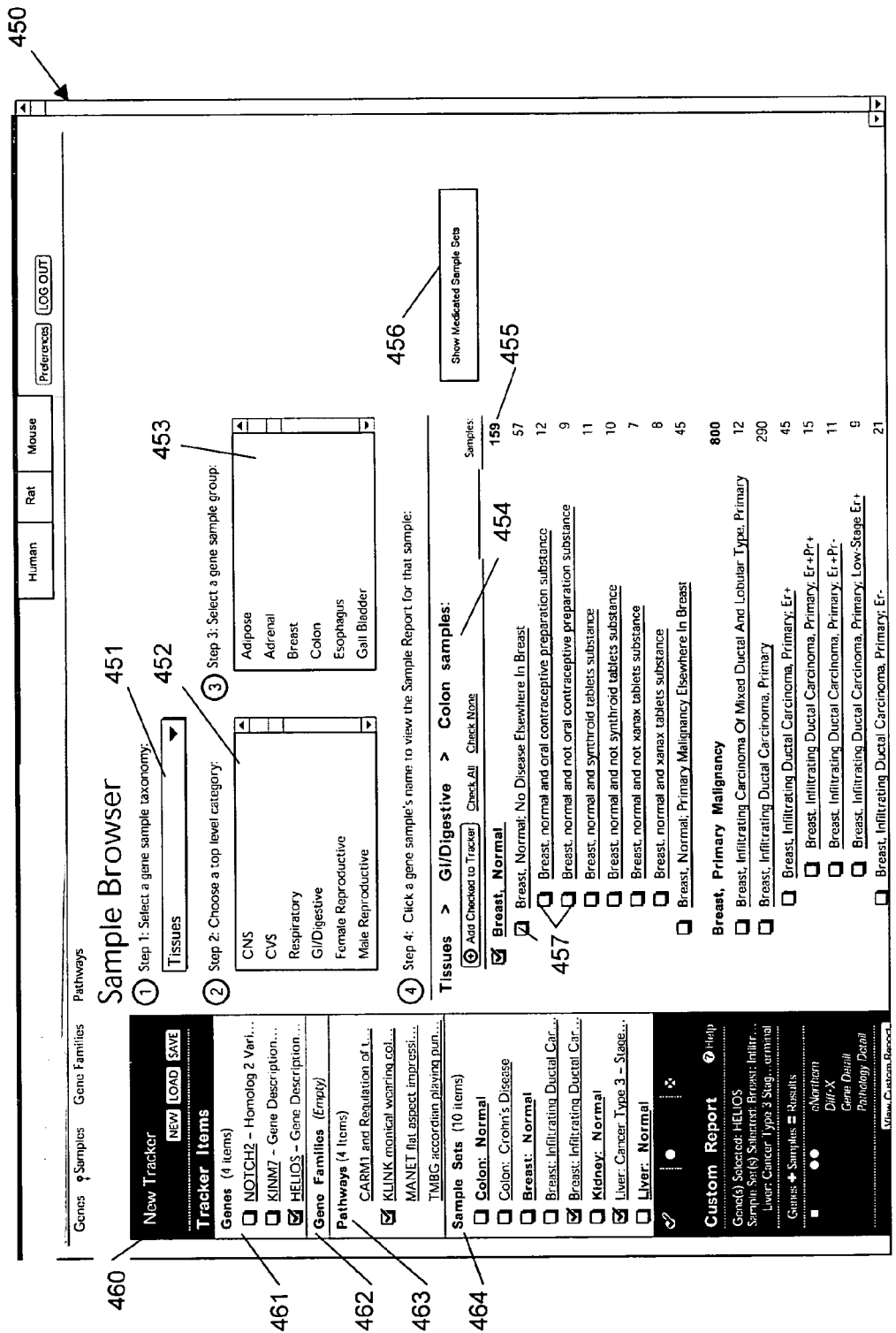
FIG. 10 illustrates an exemplary graphical user interface screen for the sample set browser.

Table 454 in FIG. 10 includes a column of numbers 455 to the right of the sample set names. This number indicates the quantity of samples within that sample set. In some cases, the number of medication sets (children of the normal parent set) will be large, forcing the user to scroll through an extensive list to view the disease sets which are of primary importance. By selecting button 456 shown with the description "Show Medicated Sample Sets", the user has option to show or hide the medication sample sets. The default is for the medication sets to be hidden when the "Tissues" and "Diseases" sort options are selected. If the user selects <show medication>, the screen will refresh and the medication sets are shown as children under the normal parent set.

Table 454 also displays a check box to the left of the each sample set name which may be used to select a sample set for placement into the "Tracker™" tracking module, which is shown at the left side of GUI screen 450 and discussed below. There are a number of gene expression questions and "in silico experiments" that a researcher may wish to explore. Examples of queries that can be answered using the present system and method include:

Given two sets of well curated and qualified tissue samples, from normal and diseased tissues or from 2 sets of pathologically-related diseased samples, what genes are differentially expressed?

For a given disease node, e.g., Secondary Malignancy of the Ovary, how is this node curated and to which other normal or disease node can it be compared with respect to human pathology and bioinformatic considerations to generate a list of differentially regulated genes?

Which genes identified in the above analysis are members of a particular gene family, for example, a proven drugable class, or a biological cell signaling pathway and what information is known about these genes in that family/pathway which can help put such results in perspective and help prioritize genes?

For a particular gene of interest, how is it regulated with respect to large scale human biology across normal tissues and related disease morphologies in a therapeutic area (i.e. cardiovascular) or even across multiple therapeutic areas?

For a particular gene, what other genes in the focus organism are similarly regulated in the therapeutic area of interest or with respect to all nodes in the entire database?

If there is a homolog of the gene of interest in another species, e.g., rat and/or mouse, what does its expression look like with respect to normal and disease nodes and can such an animal model be used as a validation tool for target/drug discovery?

What other clinical variables, e.g., medication, age, race, gender, smoking, lifestyle attributes, clinical diagnostic data, etc, influence the expression level of the gene target in certain tissue types or across all human tissues?

What is the impact of disease stage on the expression of the gene target? What are the expression levels versus normal tissue or other disease stages such as tumor staging in oncology?

For the gene of interest, what relevant literature is immediately available to learn more about what is known in the public domain?

How much patent activity has there been recently in the disease area or on the gene target or gene family?

In addition to having pre-computed nodal comparisons available, the inventive system includes the functionality for manual selection of nodes for comparison which will then be dynamically be performed "on the fly".

The user can select any of the sample nodes displayed in box 454 and request that all summary expression data be displayed for that node for all the fragments on the relevant chipset. As previously described, gene expression data are pre-computed for each sample set and stored in the corresponding sample node.

The summary expression data is preferably displayed in a tabular format as shown in the exemplary report illustrated in FIG. 13. In the illustrated example, the Sample Set Report is for Breast: Infiltrating Ductal Carcinoma—Smoking. One possible search strategy that can be used to reach this result is: taxonomy: tissue, category: female reproductive, sub-category: breast; disease: primary malignancy; infiltrating ductal carcinoma. Other strategies may also be used to reach the same sample set.

In the table, each row of the summary expression report contains data for one fragment present on the relevant chipset. The columns of the data table are as follows:

Fragment ID
Gene symbol
Gene name or description
Global present frequency
% present call
% marginal call
% absent call
mean expression value
standard deviation
median expression value Due to the large volume of data to be output, in the preferred embodiment, the information is configured for export to a useable and sortable Excel® file that can be mined as a stand alone or exported to third party tools such as Spotfire®, Partek®, GeneSpring®, etc.

In a preferred embodiment, the user interface includes a tracking module 460, or "Tracker™", shown in FIG. 8, which allows the user to save selected items in an Internet shopping cart-type of arrangement, then generate custom reports by combining items saved in the module. The tracking module provides means for intersecting sample sets with genes, gene sets, gene families or pathways to produce custom analyses relevant to the user's area of interest (e.g., disease or therapeutic area) with respect to biological information. Tracking module 460 will appear on every screen of the GUI to provide a consistently available work management tool, regardless of the content/query strategy. Items that can be saved include sample sets, genes, gene families and pathways, each of which defines a separate category within the tracking module. The report options for a given tracking module will vary depending on the items selected for the analysis. The user will typically have multiple Tracker™ tracking modules, with the number of available trackers being virtually unlimited. Each tracker will contain items for a single species. The user may save, load, delete and create new tracking modules, and may select one or more items for comparison for generating custom reports.

Figure 11:
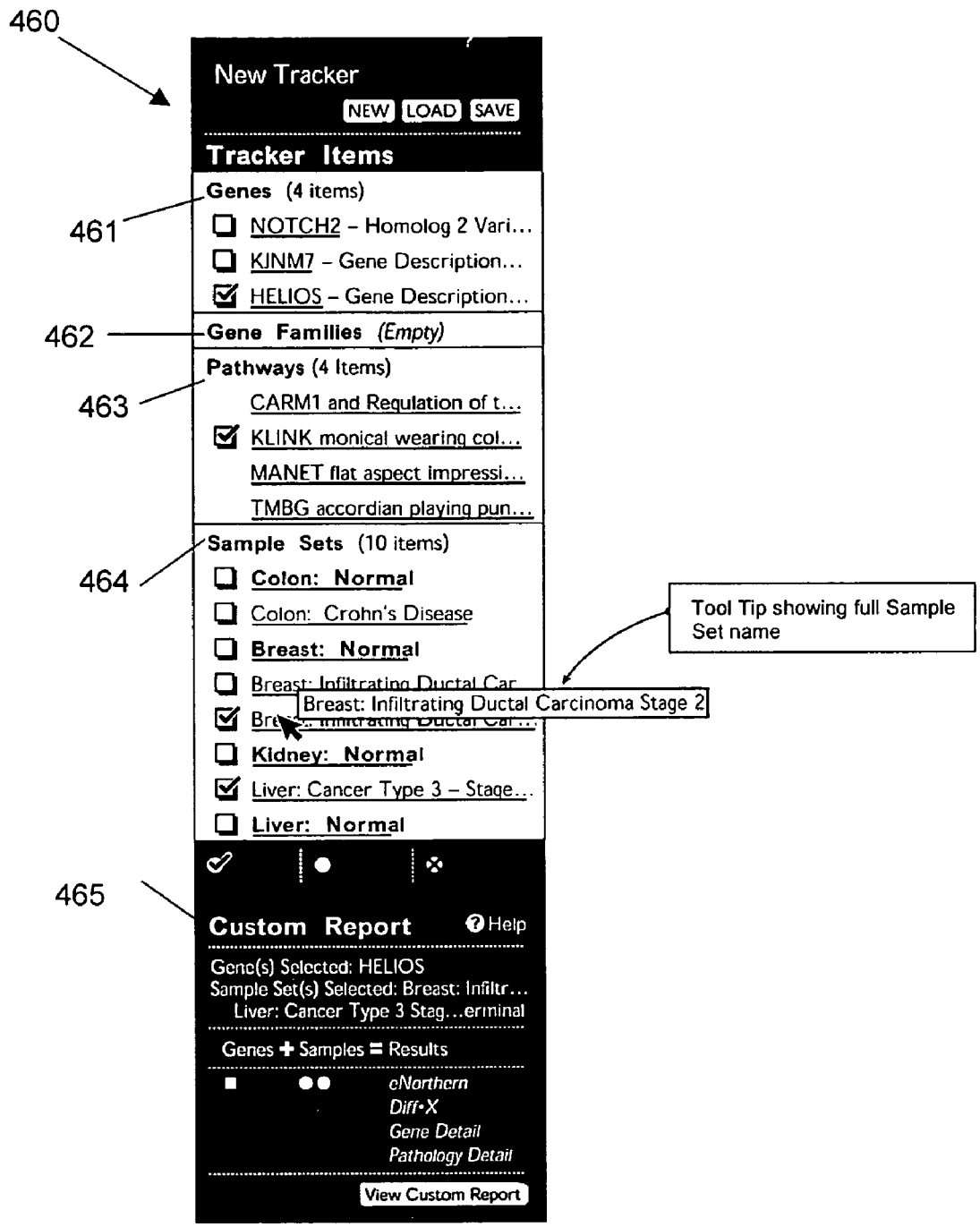
FIG. 11 shows an enlarged images of the Tracker™ module of the graphical user interface.

FIG. 11 provides an enlarged images of the Tracker™ module 460. A separate frame is provided for each query strategy, i.e., Genes (461), Gene Families (462), Pathways (463) and Sample Sets (464). Each time the user creates and saves a new Tracker™ module, the item is listed into the appropriate frame. The number of items in each frame is displayed. If a frame has no stored items, "Empty" is displayed. See, e.g., Pathway frame 463.

When the user selects a particular Tracker™ module to be loaded, the selected Tracker™ becomes the active Tracker™. The active Tracker™ is displayed in Tracker module 460.

Figure 12:
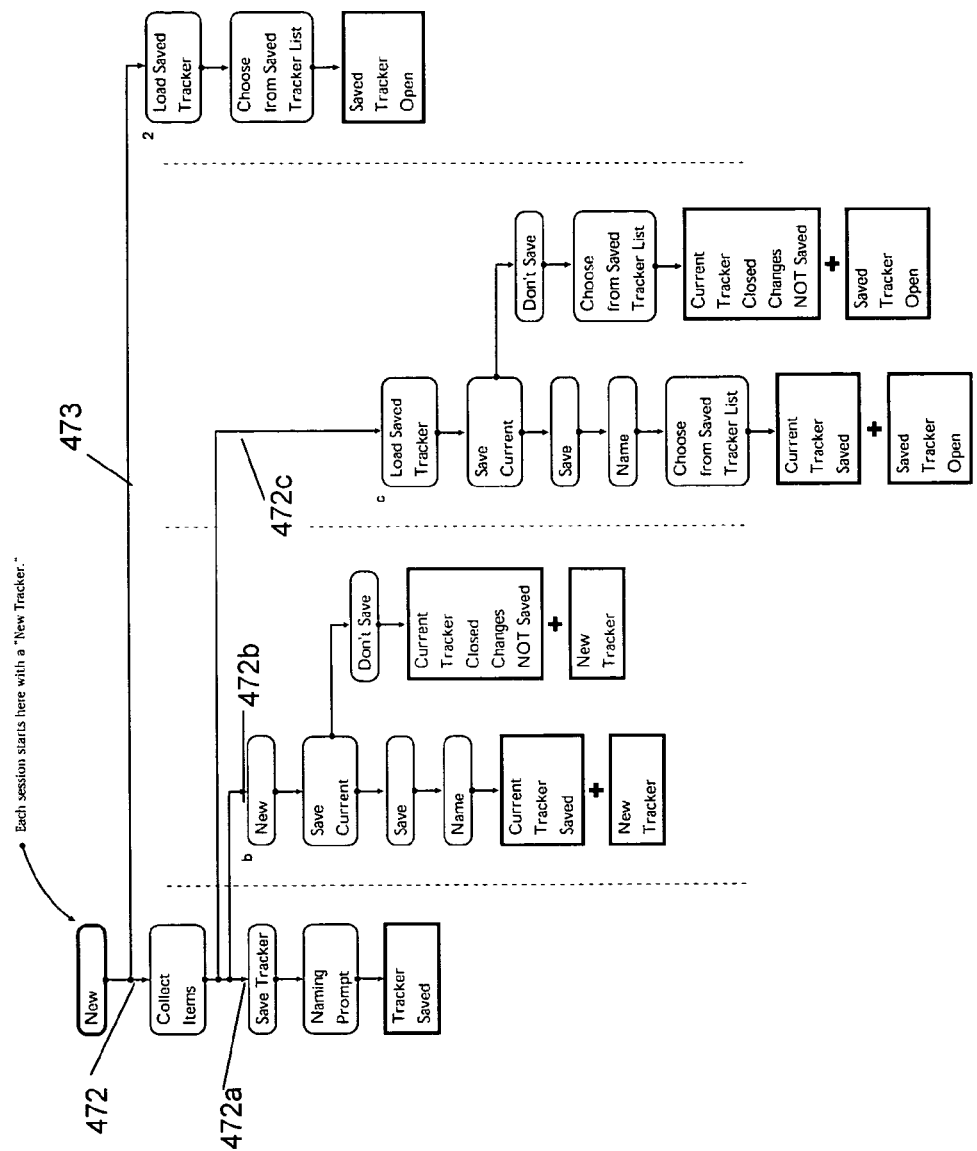
FIG. 12 provides the process flow for use of the Tracker™ module of the graphical user interface.

FIG. 12 provides the process flow for use of the Tracker™. At the start of a session, the default is to display a new, empty Tracker™ (470) in Tracker™ module 460. The user can then proceed along the first path 472 to collect items, or can select a saved Tracker™ to load and open, following path 473. If the user was previously working with a Tracker™, a query will appear on the screen asking whether he or she wishes to save the open Tracker prior to the new Tracker being opened.

If path 472 is selected, i.e., new items are to be collected, the user may follow path 472a in which, after collecting items, the items are saved in the database. The user assigns a name or other identifier to the Tracker™, and the new Tracker™ is added to the list of saved Trackers. Selection of path 472b allows the user to create a new Tracker™, save the current Tracker™, then select which Tracker™ will be displayed. The Trackers' identifiers are then displayed in the list of saved Trackers. Alternatively, the user can decide that the results of his or her query are not relevant to the area of interest and can select "Don't Save", closing the current Tracker™, then proceed with a new Tracker™ or load an existing saved Tracker™.

When following path 472c, the user loads a saved Tracker™ then saves collected items in a current Tracker™. The saved Tracker™ can then be opened for further action Alternatively, the user can decide that the collected items are not of interest and closed the current Tracker™ without saving the changes, then opening the saved Tracker™.

To select items for generation of a custom report using the Tracker™ module, the user clicks on the check box next to the item of interest. In the illustrated example in FIG. 11, the user has selected the HELIOS gene in Gene frame 461, and sample sets for "Breast, Infiltrating Ductal Carcinoma Stage 2" and "Liver Cancer Type 3" in Sample Set frame 464. These selections are displayed in "Custom Report" frame 465, which displays the possible custom analyses that are available based on the selected items.

The system and method of the present invention provides for custom analysis for Genes, Sample Sets, Gene Families and Pathways and creation of custom Gene and Sample Set reports. Table 5 below provides a few examples of custom reports that can be generated.

TABLE 5

Custom Reports

| # Genes, Gene Families or Pathways | # Sample Sets | Results (Tab Pages) |
|---|---|---|
| 1-10 Gene(s) | 1 | E-Northern (s) |
| 1-10 Gene(s) | 2 | Differential Expression (Diff/X), E-Northern (s) |
| 1-10 Gene(s) | 3-50 | E-Northern |
| ≦10 Genes | 0 | Differential Expression (Diff/X) |
| 0 | 2 | Differential Expression (Diff/X) |
| 1 Gene Family | 2 | Differential Expression (Diff/X) |
| 1 Pathway | 2 | Differential Expression (Diff/X) |

Only one gene family or pathway can be selected at a given time for generation of a Custom Report. If a gene family or pathway is selected, a gene cannot be selected. If there are no selections, the message "No current selections" is displayed.

According to the present invention, a database is provided in which gene expression and related data are either pre-calculated or computed 'on the fly' and pre-formatted, permitting automated generation of reports for genes, gene sets, gene families and pathways. The database also contains data corresponding to sample sets containing gene expression data. The sample sets are organized according to clinical relevance into sample nodes which can be readily searched according to attributes that place the sample sets into a hierarchy for convenient user display. In some cases, comparisons between sample sets can be pre-computed for producing rapid responses to searches based upon pathological or biological parameters. The data can be easily manipulated using user-selected filters and compared under user direction to produce custom reports in a significantly reduced time relative to prior art biological database mining approaches.

The following example illustrates an application of one of the gene expression pattern matching algorithms that is available as part of the present invention.

Example 3

Match/X Analysis

The Match/X algorithm was applied to identify genes that have coordinate or inverse coordinate gene expression patterns relative to CDC2. CDC2 is a key regulator of the cell cycle that is a therapeutic target for drugs designed to eliminate rapidly proliferating cells, such as those found in malignant tumors.

A gene expression database was generated using manually curated data obtained from total RNA taken from normal and diseased tissue. Target cRNA was extracted and hybridized onto Affymetrix Hu133 A/B GeneChip® arrays for gene expression analysis. Resulting gene expression data was quality tested as described above. Table 6 summarizes the content of the input data.

TABLE 6

| Therapeutic Area | Total Sets | Mean Samples | Median Samples | Min Set Size | Max Set Size |
| --- | --- | --- | --- | --- | --- |
| Total Normal | 212 | 25 | 10 | 3 | 177 |
| Total Diseased | 505 | 12 | 7 | 3 | 169 |
| Cardiovascular | 32 | 20 | 8 | 3 | 85 |
| Central Nervous | 152 | 9 | 6 | 3 | 31 |
| Metabolism | 24 | 12 | 8 | 3 | 39 |
| Oncology | 234 | 13 | 7 | 3 | 169 |
| Inflammation | 63 | 15 | 9 | 3 | 78 |

The 717 human sample sets served as the basis for 757 biologically meaningful, pairwise (disease vs. normal, and diseased vs. diseased) comparisons. The 757 pairwise comparisons are used by Match/X to identify genes with similar regulation patterns across the database.

The Match/X algorithm returned over 500 probe sets as hits to the query gene CDC2. The minimum distance score for all returned probe sets was 0.22. For biological validation of the genes with highest similarity (lowest distance), a maximum distance cutoff of 0.40 was selected (means and median distance 0.34 and 0.35, respectively), and this cutoff selected 142 probe sets for further analysis. The 142 probe sets mapped to 56 unique genes (median of 3 probe sets per gene, maximum 6), and all except for 3 unknowns were in some way related to cell cycle.

Table 7 provides a list of the low distance scoring genes identified in the Match/X results for CDC2.

TABLE 7

| Gene | Dist. | −1/−1 | −1/0 | −1/+1 | 0/−1 | 0/0 | 0/+1 | +1/−1 | +1/0 | +1/+1 |
| --- | --- | --- | --- | --- | --- | --- | --- | --- | --- | --- |
| CDC2 210559 s at | 0.22 | 4 | 3 | 0 | 2 | 659 | 11 | 0 | 17 | 61 |
| CDC2 203214 x at | 0.22 | 4 | 2 | 0 | 3 | 659 | 17 | 0 | 11 | 61 |
| CDC2 210559 s at | 0.25 | 5 | 2 | 0 | 7 | 649 | 16 | 0 | 14 | 64 |
| CDC2 203213 at | 0.25 | 5 | 7 | 0 | 2 | 649 | 14 | 0 | 16 | 64 |
| BIRC5 202095 s at | 0.25 | 2 | 5 | 0 | 4 | 661 | 13 | 0 | 13 | 59 |
| UBE2C 202954 at | 0.25 | 3 | 11 | 0 | 3 | 651 | 8 | 0 | 17 | 64 |
| HSPC150 223229 at | 0.25 | 4 | 6 | 0 | 3 | 654 | 17 | 0 | 12 | 61 |
| CCNB1 214710 s at | 0.26 | 5 | 11 | 0 | 1 | 654 | 13 | 0 | 12 | 59 |
| MAD2L1 203362 s at | 0.26 | 4 | 9 | 0 | 3 | 659 | 22 | 0 | 4 | 56 |
| KIF2C 209408 at | 0.27 | 3 | 7 | 0 | 3 | 664 | 19 | 0 | 8 | 53 |
| UBE2C 202954 at | 0.27 | 4 | 10 | 0 | 3 | 645 | 14 | 0 | 17 | 64 |
| TOP2A 201292 at | 0.27 | 8 | 8 | 0 | 4 | 643 | 19 | 0 | 14 | 61 |

Close examination of a low distance scoring gene fragment for BIRC5 (baculoviral IAP repeat-containing 5 (survivin); spindle function) reveals regulation similar to that of CDC2. BIRC5 is co-regulated with CDC2 in 61 of 757 comparisons (−1/−1 and +1/+1). In 661 comparisons, BIRC5 and CDC2 show no regulation (0/0). BIRC5 never shows inverse regulation (+1/−1 or −1/+1) with CDC2. As would be expected, fragments mapping to CDC2 show the highest similarity to each other.

It has recently been demonstrated that survivin (BIRC5) is phosphorylated and, thus, stabilized by CDC2, leading to a reduction in apoptosis in cells treated with paclitaxel, a microtubule depolymerization inhibitor. (O'Connor, et al., "A p34(cdc2) survival checkpoint in cancer", *Cancer Cell* 2002 July; 2(1):43-54.) Inhibition of CDC2 with purvalanol A greatly enhanced apoptosis in these cells while allowing a much lower dose of paclitaxel to be administered. Match/X correctly predicts a relationship between the expression of these two genes and may be a useful tool for elucidating other key relationships between expressed genes in complex biological processes such as cell cycle.

Most of the genes with expression profiles similar to CDC2 are differentially expressed during the G2 phase of the cell cycle. Approximately 48% of the 142 probe sets map to genes that are known to be differentially expressed during the G2/M phase of the cell cycle, while 12% are implicated in G2 and another 5% are differentially expressed during both G2/M and G1/S. In contrast, only about 17% of the probe sets identified map to gene with known differential expression in both G1 or S-phase.

Match/X and other gene expression pattern matching algorithms (Marker/X, Local Match/X and Normal/X) are robust and accurate pattern recognition tools for genomic data that can help discern relationships between genes with related expression patterns. The present invention provides for such analyses which may be used alone or in combination with a large number of different analytical techniques to provide researchers a wide variety of different approaches for in silico biological discovery.

In the foregoing specification, the invention has been described with reference to specific exemplary embodiments thereof. It will, however, be evident that various modifications and changes may be made thereunto without departing from the broader spirit and scope of the invention as set forth in the appended claims and their full scope of equivalents.

What is claimed is:

1. In a computer network, a method for determining patterns within gene expression data stored in a database containing biological data, the method comprising:
    (a) defining a plurality of sample nodes within the database, each sample node comprising a curated data set comprising a set of pre-formatted and pre-computed biological data obtained from at least one biological sample, wherein the plurality of sample nodes are organized in a hierarchical arrangement according to clinical relevance;
    (b) assigning a set of clinical attributes to each sample node, the set of clinical attributes including at least one taxonomy designation selected from the group consisting of tissues, diseases, medications and sample parameters;
    (c) providing a user interface for entry of a search query into the computer processor and displaying search results at a user interface;
    (d) prompting entry of the search query by requesting user selection of a search category from the group consisting of biological materials, biological material family, biological pathways, and sample set taxonomy, and wherein each sample node of the plurality of sample nodes is associated with a plurality of search categories;
    (e) searching the plurality of sample nodes for data responsive to the search query;
    (f) selecting one or more sample nodes containing the data responsive to the search query;
    (g) saving search results comprising the set of pre-formatted and pre-computed biological data responsive to the one or more selected sample nodes;
    (h) receiving a user interface selection of an algorithm for performing gene expression pattern matching for identifying genes or gene fragments within the one or more selected sample nodes that have similar gene expression patterns to a gene of interest, the algorithm comprising:
        (i) computing a plurality of pairwise comparisons between the gene of interest and the genes or gene fragments within the one or more sample nodes, wherein each comparison is encoded using a qualitative three-state encoding scheme, wherein up-regulation of gene expression in the gene of interest relative to the genes or gene fragments within the one or more sample nodes is assigned a first symbol, down-regulation of gene expression in the gene of interest relative to the genes or gene fragments within the one or more sample nodes is assigned a second symbol different from the first symbol and no change in gene expression in the gene of interest relative to the genes or gene fragments within the one or more sample nodes is assigned a third symbol different from the first and second symbols wherein the three-state encoding scheme comprises a non-quantitative indication of gene behavior;
        (ii) generating a three-by-three contingency matrix for each pairwise comparison using the three-state encoding scheme;
        (iii) determining a distance score for each pairwise comparison;
        (iv) generating a listing of lowest distance scores, wherein the lowest distance scores correspond to genes or gene fragments having the highest similarity to the gene of interest; and
    (i) generating an output display comprising the listing of genes or gene fragments having the lowest distance scores.

2. The method of claim 1, wherein the biological materials search category is selected from the group consisting of genes, proteins, metabolites and biomolecular assay.

3. The method of claim 1, wherein the gene expression pattern matching algorithm identifies co-regulated and inverse co-regulated gene expression patterns relative to the gene of interest.

4. The method of claim 3, wherein the algorithm is adapted to identify coordinate or inverse coordinate gene expression patterns within a specified therapeutic area.

5. The method of claim 3, wherein the algorithm is adapted to identify coordinate or inverse coordinate gene expression patterns across normal tissues.

6. The method of claim 2, wherein the selected search category is biological material family, wherein the biological material family comprises a gene family, and wherein the search report further comprises differential expression for gene family members and a listing of gene family members.

7. The method of claim 1, wherein the selected search category is biological pathway and the search report further comprises differential expression for pathway-linked expressed entities and a listing of member expressed entities of the biological pathway.

8. The method of claim 1, wherein the selected search category is sample set taxonomy, wherein the search query comprises:

selecting a taxonomy designation,
selecting a category from a plurality of categories within the selected taxonomy designation; and
selecting a sub-category from a plurality of sub-categories within the selected category, wherein each sub-category comprises a group of sample nodes having attributes corresponding to the selected taxonomy designation, selected category and the selected sub-category.

9. The method of claim 8, wherein the selected taxonomy comprises tissues and the plurality of categories comprises organ systems.

10. The method of claim 9, wherein the category is selected from the organ system group consisting of cardiovascular system, central nervous system, GI/digestive system, respiratory system, reproductive system, skeletal system, endocrine system, excretory system, skeletal system, and muscular system.

11. The method of claim 9, wherein the plurality of sub-categories are tissue types and the group of sample nodes comprises disease data.

12. The method of claim 9, wherein the search query comprises a tissue of interest.

13. The method of claim 8, wherein the selected taxonomy comprises diseases and the plurality of categories comprises therapeutic areas.

14. The method of claim 13, wherein the therapeutic areas comprise oncology/cancer, cardiovascular diseases, inflammation disorders, central nervous system disorders and metabolic diseases.

15. The method of claim 13, wherein the selected therapeutic area comprises oncology/cancer and the sub-categories comprise types of cancer.

16. The method of claim 13, wherein the plurality of sub-categories comprises disease types and the group of sample nodes comprises tissue data.

17. The method of claim 8, wherein the selected taxonomy comprises medications and the plurality of categories comprises medication.

18. The method of claim 17, wherein the plurality of sub-categories comprises tissue type and the group of sample nodes comprises tissue data.

19. The method of claim 1, further comprising:
storing a text description of each sample node in the database;
within the database, associating the text description with each sample node.

20. The method of claim 1, wherein the user interface comprises an Internet web site and each search category has a corresponding distinct web page.

21. The method of claim 1, further comprising:
pre-computing a plurality of pairwise node comparisons between two different sample nodes for a subset of the plurality of sample nodes, comprising:
selecting the subset from sample nodes having a pathological relationship with at least one other sample node in the subset;
comparing gene expression data within the two different sample nodes to determine a differential expression between the two different sample nodes;
storing the plurality of pairwise node comparisons in the database; and
associating each pairwise node comparison with each of its corresponding sample nodes.

22. The method claim 21, wherein the subset of sample nodes is user selected and the step of computing is performed on-the-fly.

23. The method of claim 21, wherein the pairwise node comparison comprises comparison of sample nodes selected from the group consisting of normal versus disease, morphologies of two different diseases, normal versus normal on different tissues, normal versus secondary malignancy, and primary versus secondary malignancy.

24. The method of claim 1, further comprising:
providing a tracking module for saving search results;
repeating steps (d) through (g) for a plurality of iterations;
prompting the user to save in the tracking module selected search results corresponding to at least a portion of the plurality of iterations;
prompting the user to select one or more search results saved in the tracking module.

25. The method of claim 1, further comprising associating at least one histopathology image with each sample node.

26. A network-based system for determining patterns within gene expression data stored in a database containing biological data, the system comprising:
a processor including a search engine;
a database comprising:
a plurality of sample nodes, each sample node comprising a curated data set comprising a set of pre-formatted and pre-computed biological data obtained from at least one biological sample, wherein the plurality of sample nodes are organized in a hierarchical arrangement according to clinical relevance;
a set of clinical attributes assigned to each sample node, the set of clinical attributes including at least one taxonomy designation selected from the group consisting of tissues, diseases, medications and sample parameters;
a user interface to enter a search query and display search results, wherein the search query comprises an instruction to the search engine to search a category from the group consisting of biological materials, biological material families, biological pathways, and sample set taxonomy, and wherein each sample node of the plurality of sample nodes is associated with a plurality of search categories; and
a tracking module for storing data corresponding to a plurality of user selected sample nodes and further comprising means for receiving a user interface selection of an algorithm to be executed by the processor for performing gene expression pattern matching for identifying genes or gene fragments within the user selected sample nodes that have similar gene expression patterns to a gene of interest, wherein the algorithm comprises the steps of:
(i) computing a plurality of pairwise comparisons between the gene of interest and the genes or gene fragments within the user selected sample nodes, wherein each comparison is encoded using a qualitative three-state encoding scheme, wherein up-regulation of gene expression in the gene of interest relative to the genes or gene fragments within the one or more sample nodes is assigned a first symbol, down-regulation of gene expression in the gene of interest relative to the genes or gene fragments within the one or more sample nodes is assigned a second symbol different from the first symbol and no change in gene expression in the gene of interest relative to the genes or gene fragments within the one or more sample nodes is assigned a third symbol different from the first and second symbols wherein the three-state encoding scheme comprises a non-quantitative indication of gene behavior;

(ii) generating a three-by-three contingency matrix for each pairwise comparison using the three-state encoding scheme;
(iii) determining a distance score for each pairwise comparison;
(iv) generating a listing of lowest distance scores, wherein the lowest distance scores correspond to genes or gene fragments having the highest similarity to the gene of interest; and
(v) displaying the listing of the lowest distance scores and the corresponding genes or gene fragments.

27. The system of claim 26, wherein the user selected sample nodes comprises sample nodes having a pathological relationship with at least one other sample node in the subset.

28. The system of claim 27, wherein the user selected sample nodes are selected from the group consisting of normal versus disease, morphologies of two different diseases, normal versus normal on different tissues, normal versus secondary malignancy, and primary versus secondary malignancy.

29. The system of claim 26, wherein the tracking module further comprises means for requesting on-the-fly custom pairwise node comparison of two stored sample nodes.

30. The system of claim 26, wherein the tracking module further comprises means for generation of one or more additional reports selected from the group consisting of gene detail, eNorthern, differential expression, pathology report, and time study, using one or more user selected sample nodes.

31. The system of claim 26, wherein the user interface comprises an Internet web site and each search category has a corresponding web page.

32. The system of claim 26, wherein the biological material search category comprises the group consisting of genes, proteins, metabolites and biomolecular assay.

33. The system of claim 26, wherein the search category is sample set taxonomy and the search query further comprises:
a first user selection of taxonomy designation;
a second user selection of a category from a plurality of categories within the selected taxonomy designation;
a third user selection of a sub-category from a plurality of sub-categories within the selected category, wherein each sub-category comprises a group of sample nodes having attributes corresponding to the selected taxonomy designation, the selected category and the selected sub-category.

34. The system of claim 33, wherein the taxonomy designation is tissues and the plurality of categories comprises organ systems.

35. The system of claim 34, wherein the search query comprises a tissue of interest and further comprising executing a gene expression pattern matching algorithm for identifying marker genes expressed in the tissue of interest.

36. The system of claim 34, wherein the selected category is selected from the organ system group consisting of cardiovascular system, central nervous system, GI/digestive system, respiratory system, reproductive system, skeletal system, endocrine system, excretory system, skeletal system, and muscular system.

37. The system of claim 36, wherein the plurality of sub-categories are tissue types and the group of sample nodes comprises disease data.

38. The system of claim 33, wherein the taxonomy designation comprises diseases and the plurality of categories comprises therapeutic areas.

39. The system of claim 38, wherein the therapeutic areas comprise oncology/cancer, cardiovascular diseases, inflammation disorders, central nervous system disorders and metabolic diseases.

40. The system of claim 39, wherein the selected therapeutic area comprises oncology/cancer and the sub-categories comprise types of cancer.

41. The system of claim 39, wherein the plurality of sub-categories comprises disease types and the group of sample nodes comprises tissue data.

42. The system of claim 33, wherein the taxonomy designation comprises medications and the plurality of categories comprises medication.

43. The system of claim 42, wherein the plurality of sub-categories comprises tissue type and the group of sample nodes comprises tissue data.

44. The system of claim 26, wherein the database further comprises at least one histopathology image associated with each sample node.

45. The system of claim 26, wherein the gene expression pattern matching algorithm identifies co-regulated and inverse co-regulated gene expression patterns relative to the gene of interest.

46. The system of claim 26, wherein the algorithm is adapted to identify co-regulated and inverse co-regulated gene expression patterns within a specified therapeutic area.

47. The system of claim 26, wherein the algorithm is adapted to identify co-regulated and inverse co-regulated gene expression patterns across normal tissues.

48. The system of claim 26, wherein the selected search category is biological material family, the biological material family is gene family, and the search report further comprises differential expression for gene family members and a listing of gene family members.

49. The system of claim 26, wherein the selected search category is biological pathway and the search report further comprises differential expression for pathway-linked genes and a listing of member expressed entities of the biological pathway.

* * * * *

UNITED STATES PATENT AND TRADEMARK OFFICE
CERTIFICATE OF CORRECTION

PATENT NO. : 7,428,554 B1  Page 1 of 1
APPLICATION NO. : 10/850232
DATED : September 23, 2008
INVENTOR(S) : Carter Coberly et al.

It is certified that error appears in the above-identified patent and that said Letters Patent is hereby corrected as shown below:

On the title page, item [75] inventors: "Coberley" should read --Coberly--.

Signed and Sealed this

Seventeenth Day of February, 2009

JOHN DOLL
*Acting Director of the United States Patent and Trademark Office*